(12) United States Patent
Ouyang et al.

(10) Patent No.: US 9,775,549 B2
(45) Date of Patent: Oct. 3, 2017

(54) TEMPERATURE INSENSITIVE IN VIVO ANALYTE DEVICES, METHODS AND SYSTEMS

(71) Applicant: Abbott Diabetes Care Inc., Alameda, CA (US)

(72) Inventors: Tianmei Ouyang, Fremont, CA (US); Benjamin J. Feldman, Berkeley, CA (US); Udo Hoss, Castro Valley, CA (US); Balasubrahmanya S. Bommakanti, Pleasanton, CA (US); Gurinder Sandhu, Fairfield, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 112 days.

(21) Appl. No.: 14/737,082

(22) Filed: Jun. 11, 2015

(65) Prior Publication Data
US 2016/0045147 A1 Feb. 18, 2016

Related U.S. Application Data

(60) Provisional application No. 62/038,071, filed on Aug. 15, 2014.

(51) Int. Cl.
| A61B 5/1455 | (2006.01) |
| A61B 5/05 | (2006.01) |
| A61B 5/1486 | (2006.01) |
| A61B 5/00 | (2006.01) |
| A61B 5/145 | (2006.01) |

(52) U.S. Cl.
CPC ...... *A61B 5/14865* (2013.01); *A61B 5/14532* (2013.01); *A61B 5/686* (2013.01)

(58) Field of Classification Search
None
See application file for complete search history.

(56) References Cited

U.S. PATENT DOCUMENTS

| 5,254,668 | A | 10/1993 | Dominguez et al. |
| 5,262,035 | A | 11/1993 | Gregg et al. |
| 5,262,305 | A | 11/1993 | Heller et al. |
| 5,264,104 | A | 11/1993 | Gregg et al. |
| 5,320,725 | A | 6/1994 | Gregg et al. |
| 5,356,786 | A | 10/1994 | Heller et al. |
| 6,121,009 | A | 9/2000 | Heller et al. |
| 6,134,461 | A | 10/2000 | Say et al. |
| 6,175,752 | B1 | 1/2001 | Say et al. |
| 6,514,718 | B2 | 2/2003 | Heller et al. |
| 6,560,471 | B1 | 5/2003 | Heller et al. |
| 6,579,690 | B1 | 6/2003 | Bonnecaze et al. |
| 6,592,745 | B1 | 7/2003 | Feldman et al. |
| 6,600,997 | B2 | 7/2003 | Deweese et al. |
| 6,605,200 | B1 | 8/2003 | Mao et al. |
| 6,605,201 | B1 | 8/2003 | Mao et al. |
| 6,736,957 | B1 | 5/2004 | Forrow et al. |
| 6,881,551 | B2 | 4/2005 | Heller et al. |
| 6,932,894 | B2 | 8/2005 | Mao et al. |
| 7,299,082 | B2 | 11/2007 | Feldman et al. |
| 7,501,053 | B2 | 3/2009 | Karinka et al. |
| 7,811,231 | B2 | 10/2010 | Jin et al. |
| 8,106,780 | B2 | 1/2012 | Goodnow et al. |
| 8,601,465 | B2 | 12/2013 | Bernstein et al. |
| 9,014,774 | B2 * | 4/2015 | Mao .................. A61B 5/14532 600/347 |
| 9,380,965 | B2 * | 7/2016 | Ouyang ............ A61B 5/14532 |
| 2003/0042137 | A1 | 3/2003 | Mao et al. |
| 2005/0173245 | A1 | 8/2005 | Feldman et al. |
| 2010/0063374 | A1 | 3/2010 | Goodnow et al. |
| 2010/0086678 | A1 | 4/2010 | Arthur et al. |
| 2010/0198034 | A1 | 8/2010 | Thomas et al. |
| 2010/0213057 | A1 | 8/2010 | Feldman et al. |
| 2010/0324392 | A1 | 12/2010 | Yee et al. |
| 2010/0326842 | A1 | 12/2010 | Mazza et al. |
| 2011/0120865 | A1 | 5/2011 | Bommakanti et al. |
| 2011/0213225 | A1 | 9/2011 | Bernstein et al. |
| 2011/0256024 | A1 | 10/2011 | Cole et al. |
| 2011/0257495 | A1 | 10/2011 | Hoss et al. |
| 2012/0157801 | A1 | 6/2012 | Hoss et al. |
| 2012/0245447 | A1 | 9/2012 | Karan et al. |
| 2012/0296186 | A1 | 11/2012 | Ouyang et al. |
| 2012/0323098 | A1 | 12/2012 | Moein et al. |

* cited by examiner

*Primary Examiner* — Ana Woodward
(74) *Attorney, Agent, or Firm* — Edward J. Baba; Khin K. Chin; Bozicevic, Field & Francis LLP

(57) ABSTRACT

Disclosed herein are membrane structures for use in analyte sensors, where the membrane structures exhibit low temperature sensitivity.

10 Claims, 15 Drawing Sheets

TEMPERATURE INSENSITIVE IN VIVO ANALYTE DEVICES, METHODS AND SYSTEMS

CROSS-REFERENCE TO RELATED APPLICATION

This application claims priority based on U.S. Provisional Application No. 62/038,071, filed Aug. 15, 2014, the disclosure of which is incorporated by reference herein in its entirety.

INTRODUCTION

The characterization of analytes in biological fluids has become an integral part of medical diagnoses and assessments of overall health and wellness of a patient. Regularly monitoring the concentration of particular analytes in body fluid of a subject is becoming increasingly important where the results may play a prominent role in the treatment protocol of a patient in a variety of disease conditions. Glucose may be monitored, for example. In response to this growing importance of analyte monitoring, a variety of analyte detection protocols and devices for laboratory, point-of-care and at-home use have been developed. U.S. Patent Application No. US2011/0213225 and U.S. Pat. No. 6,175,752, which disclose in vivo analyte monitoring systems. But in vivo analyte monitoring systems can be negatively impacted by temperature. For example, many enzymes and/or other components of in vivo analyte systems are sensitive to changes in temperature, and can therefore provide different analyte information at different temperatures, and can also provide inaccurate analyte information when subjected to certain temperatures. Glucose oxidase for the detection and/or concentration of glucose in bodily fluid is an example. Given the importance of accurate analyte testing systems such as in vivo glucose testing systems, it is surprising that some in vivo analyte systems do not monitor assay temperature, let alone attempt to correct for it.

While in vivo analyte monitoring is desirable, there are challenges associated with biosensors constructed for in vivo use. Accordingly, further development of improved analyte sensors and methods of in vivo analyte monitoring having a higher degree of accuracy, stability and reduced variability in signal over an extended period of time is desirable, especially those that are immune to temperature changes such as in vivo temperature changes, for example.

SUMMARY

Disclosed herein are in vivo analyte monitoring devices, systems and methods that are temperature insensitive to analyte permeability at least at temperatures for which the insensitive in vivo analyte monitoring devices, systems and methods are or could be exposed (SMART devices, systems and methods), such as in vivo use temperatures like room temperatures, mammalian body temperatures, and the like. Included are in vivo analyte flux limiting membrane structures that are temperature insensitive to the rate of permeability of at least one analyte, at least at temperatures for which they are or could be exposed (SMART membranes), such as in vivo use temperatures like room temperatures, mammalian body temperatures, and the like. The SMART membranes regulate the permeability of analyte (e.g., glucose) through the membrane at different temperatures to maintain a constant permeability over a range of temperatures, and minimize or in some instances eliminate changes in sensitivity values of the in vivo analyte sensor with which the SMART membranes are used. In other words, the SMART membranes control the rate of analyte through the membranes to the working electrode active area so the rate is the same over a wide range of use temperatures, or at least has a standard deviation that does not have statistically significant clinical relevance. For example, analyte flux through the SMART membranes remains constant or at least changes are small enough to remain clinically insignificant at temperatures from 20° C. to 60° C., such as from 25° C. to 50° C. As such, the clinically insignificant change of flux of analyte through the SMART membranes results in little to no change (increase or decrease) in sensor response to changes in temperature over at least these temperature ranges, where the analyte flux rate changes by 5% or less per degree Celsius, such as 2% or less per degree Celsius, and including where analyte flux rate does not change at all (i.e., 0% change) in response to a change in temperature.

In some embodiments, the SMART membranes are composed of one or more polymers having a heterocyclic nitrogen containing component and a polyetheramine crosslinker. In some embodiments, the SMART membranes include a heterocyclic nitrogen containing polymer, polyetheramine, glycidyl ether and polyethylene glycol. In other embodiments, the SMART membranes are composed of a polymer having a backbone that includes a polymer with a heterocyclic nitrogen containing component, and a copolymer of polyethylene oxide and polypropylene oxide. In some embodiments, SMART membranes include a heterocyclic nitrogen containing polymer, polyethylene oxide and polypropylene oxide copolymer, glycidyl ether and polyethylene glycol.

Also disclosed are SMART in vivo analyte sensors (e.g., in vivo analyte sensors used in continuous glucose monitoring or Flash glucose monitoring systems), devices, systems and methods that include an enzyme component and a SMART membrane proximate to the enzyme component, e.g., on top of or around at least a portion of the enzyme component.

BRIEF DESCRIPTION OF THE DRAWINGS

A detailed description of various embodiments of the present disclosure is provided herein with reference to the accompanying drawings, which are briefly described below. The drawings are illustrative and are not necessarily drawn to scale. The drawings illustrate various embodiments of the present disclosure and may illustrate one or more embodiment(s) or example(s) of the present disclosure in whole or in part. A reference numeral, letter, and/or symbol that is used in one drawing to refer to a particular element may be used in another drawing to refer to a like element.

DETAILED DESCRIPTION

Figure 1:
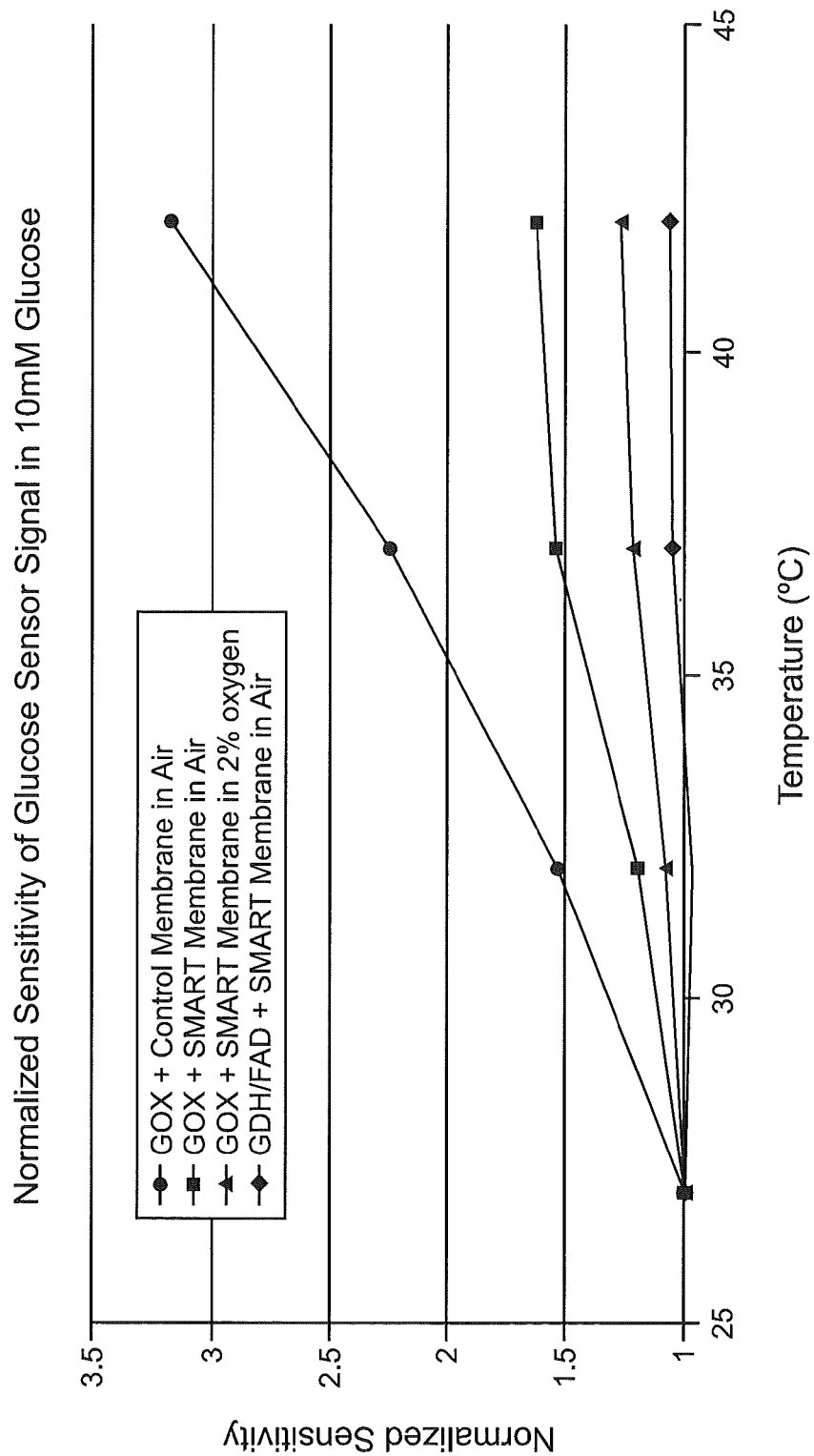
FIG. 1 shows a graph of normalized signal sensitivity as a function of temperature comparing glucose sensors employing a SMART membrane having a poly(4-vinylpyridine-co-styrene) polymer and polyetheramine crosslinker and a glucose sensor employing a poly(4-vinylpyridine-co-styrene) polymer control membrane.

Before the embodiments of the present disclosure are described, it is to be understood that this invention is not limited to particular embodiments described, as such may, of course, vary. It is also to be understood that the terminology used herein is for the purpose of describing particular embodiments only, and is not intended to be limiting, since the scope of the embodiments of the invention will be defined by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

In the description of the invention herein, it will be understood that a word appearing in the singular encompasses its plural counterpart, and a word appearing in the plural encompasses its singular counterpart, unless implicitly or explicitly understood or stated otherwise. Merely by way of example, reference to "an" or "the" "analyte" encompasses a single analyte, as well as a combination and/or mixture of two or more different analytes, reference to "a" or "the" "concentration value" encompasses a single concentration value, as well as two or more concentration values, and the like, unless implicitly or explicitly understood or stated otherwise. Further, it will be understood that for any given component described herein, any of the possible candidates or alternatives listed for that component, may generally be used individually or in combination with one another, unless implicitly or explicitly understood or stated otherwise. Additionally, it will be understood that any list of such candidates or alternatives, is merely illustrative, not limiting, unless implicitly or explicitly understood or stated otherwise.

Various terms are described below to facilitate an understanding of the invention. It will be understood that a corresponding description of these various terms applies to corresponding linguistic or grammatical variations or forms of these various terms. It will also be understood that the invention is not limited to the terminology used herein, or the descriptions thereof, for the description of particular embodiments. Merely by way of example, the invention is not limited to particular analytes, bodily or tissue fluids, blood or capillary blood, or sensor constructs or usages, unless implicitly or explicitly understood or stated otherwise, as such may vary.

The present disclosure includes SMART membranes, devices, methods and in vivo analyte sensors. The terms SMART membranes, SMART devices, SMART methods and SMART in vivo analyte sensors mean that the subject membranes, devices, methods and sensors are temperature independent and therefore regulate the permeability of at least one analyte through the membrane over a range of temperatures so that the analyte concentration is not adversely influences by the changing temperature. The analyte permeability through the membrane remains constant or clinically insignificant (little to no increase or decrease changes) over a range of temperatures. The SMART sensor devices disclosed throughout therefore have sensor sensitivities throughout temperature ranges that are constant to within tight standard deviations. In other words, subject membranes, devices, methods and sensors have rates of analyte diffusion (i.e., analyte flux) through analyte limiting membranes that show little to no change (i.e., increase or decrease) at different temperatures and/or in response to a change in temperature. Temperature insensitivity, constant or the same analyte permeability, low temperature sensitivity, temperature independent and analogous terms are used herein interchangeably. Temperature insensitivity is a rate of analyte diffusion through an analyte permeable membrane that does not change (increase or decrease) by more than 5% per ° C., such as by 4.5% per ° C., 4.0% per ° C., 3.5% per ° C., 3.0% per ° C., 2.5% per ° C., 2.0% per ° C., 1.5% per ° C., 1.0% per ° C., 0.5% per ° C., 0.01% or less per ° C., in response to changes in temperatures of 20° C. to 60° C. with a standard deviation of about 1%. The rate of analyte such as glucose across a SMART membranes is constant (within the parameters mentioned herein) over a temperature range such as from 20° C. to 60° C., or 25° C. to 50° C., including at temperatures of 27° C., 37° C., 47° C. and 57° C. In other words, SMART membranes exhibit the same rate of analyte diffusion through the membrane over temperatures from 20° C. to 60° C. In some embodiments, the rate of analyte diffusion through SMART membranes does not change at all (i.e., 0% change) in response to a change in temperature.

In some embodiments, SMART flux limiting membranes resist changes in analyte permeability for an extended period of time. For example, SMART membranes buffer changes in analyte permability for at least the in vivo lifetime (wear time or use time) of the SMART membrane or SMART sensor with which it is used. The temperature insensitive period may be 1 day a year or more, for example may be 14 days or more.

The thickness of the SMART membranes described herein and when used with in vivo glucose sensors range from 0.1 µm to 1000 µm, such as from 1 µm to 500 µm and including from 10 µm to 100 µm. In certain embodiments, the thickness of SMART membranes is 30 µm. In some embodiments, the thickness does not vary across the area of a membrane, e.g., the thickness has a c.v. of 20% or less.

When used to detect and/or monitor analyte such as glucose, the SMART membranes are positioned proximate to an enzyme component and limit passage of one or more analytes from an area away from the enzyme to the enzyme over a predetermined temperature range or changes in temperature, so that the rate of analyte diffusion through the SMART membrane to the enzyme is immune the temperature changes of the membrane's environment changes. In embodiments in which SMART membranes are used with an in vivo analyte sensor to form a SMART analyte sensor, the change in the flux of the analyte to the sensor's active area such as to a working electrode in an electrochemical sensor is resisted over changes in temperature, so that the sensor is linearly responsive over a large range of analyte concentration, e.g., 40 mg/dL to 500 mg/dL for glucose monitoring over a range of temperatures.

Analytes include a substance or chemical constituent in a fluid such as a biological fluid (for example, saliva, whole blood, tears, interstitial fluid, dermal fluid, cerebral spinal fluid, lymph fluid or urine) that can be analyzed. Analytes can include naturally occurring substances, artificial substances, metabolites, and/or reaction products. Analyte can be naturally present in the biological fluid or endogenous; for example, a metabolic product, a hormone, an antigen, an antibody, and the like. Analytes may be introduced into the body or exogenous, for example, a contrast agent for imaging, a radioisotope, a chemical agent, a fluorocarbon-based synthetic blood, or a drug or pharmaceutical composition, including but not limited to insulin, and metabolites or byproducts thereof. Analytes may also include metabolic products of drugs and pharmaceutical compositions. Analytes may include glucose, lactate, salts, sugars, proteins fats, vitamins and hormones naturally occurring in blood, dermal fluids, or interstitial fluids. In certain embodiments, an analyte of interest is glucose. Embodiments include SMART membranes or a plurality of membranes that limit the flux of more than one analyte at the same time.

SMART membranes include polymeric membranes having a diffusivity which exhibits low temperature sensitivity. The term "polymer" is used in its conventional sense to refer to molecular structures (e.g., a macromolecule) that include repeating structural units (e.g., monomers). These subunits are typically connected by covalent chemical bonds. Polymers may be branched or unbranched. Polymers may be homopolymers, which are polymers formed by polymerization of a single type of monomer. In other embodiments, polymers are heteropolymers (e.g., copolymers) that include two or more different types of monomers. Copolymers can have alternating monomer subunits, or in some cases, may be block copolymers, which include two or more homopolymer subunits linked by covalent bonds. For example, block copolymers with two blocks of two distinct chemical species (e.g., A and B) are called diblock copolymers, and block copolymers with three blocks of two distinct chemical species (e.g., A and B) are called triblock copolymers.

In certain embodiments, polymers include one or more crosslinker (crosslinking agent) such that the polymeric backbones are crosslinked. A "crosslinker" is a molecule that contains at least two reactive groups capable of linking at two or more polymers together or linking two or more portions of the same polymer together. As described herein, linking two or more different polymers together is intermolecular crosslinking, whereas linking two more portions of the same polymer is intramolecular crosslinking. In embodiments of the present disclosure, crosslinkers of interest may be capable of both intermolecular and intramolecular crosslinkings at the same time.

Flux limiting SMART membranes according to certain embodiments can include one or more polymers and one or more crosslinkers. In some cases, the one or more polymers and one or more crosslinkers form a SMART flux limiting membrane that includes a crosslinked polymer.

As mentioned, in certain embodiments SMART membranes have the same diffusivity to a given analyte (e.g., glucose) over a predetermined temperature range. In some instances, the rate of analyte diffusion through the SMART membrane depends on the lower critical solution temperature (LCST) of the membrane. The term "low critical solution temperature" is used herein in its conventional sense to refer to the temperature below which the components of a mixture are miscible. For example, the LCST may depend on pressure (e.g., increasing pressure may increase the LCST), degree of polymerization, polydispersity (e.g., the distribution of molecular mass in the polymer), branching of the polymer, and the like. At temperatures above the LCST, one or more polymers may be immiscible (e.g., one or more polymers may solidify or crystalize), which may result in a decrease in analyte diffusion through the membrane. In some instances, this decrease in the diffusivity of the flux limiting membrane may offset the increase in diffusivity due to increasing the temperature, such that the flux limiting membrane has the same diffusivity to solutes (e.g., glucose) over a temperature range of interest.

The temperature insensitive SMART membranes may include a heterocycle-containing component. The term heterocycle (also referred to as "heterocyclcyl") is used herein in its conventional sense to refer to any cyclic moiety which includes one or more heteroatoms (i.e., atoms other than carbon) and may include, but are not limited to N, P, O, S, Si, etc. Heterocycle-containing polymers may be heteroalkyl, heteroalkanyl, heteroalkenyl and heteroalkynyl as well as heteroaryl or heteroarylalkyl.

"Heteroalkyl, Heteroalkanyl, Heteroalkenyl and Heteroalkynyl" by themselves or as part of another substituent refer to alkyl, alkanyl, alkenyl and alkynyl groups, respectively, in which one or more of the carbon atoms (and any associated hydrogen atoms) are independently replaced with the same or different heteroatomic groups. Typical heteroatomic groups which can be included in these groups include, but are not limited to, —O—, —S—, —S—S—, —O—S—, —NR$^{37}$R$^{38}$, =N—N=, —N=N—, —N=N—NR$^{39}$R$^{40}$, —PR$^{41}$—, —P(O)$_2$—, —POR$^{42}$—, —O—P(O)$_2$—, —S—O—, —S—(O)—, —SO$_2$—, —SnR$^{43}$R$^{44}$— and the like, where R$^{37}$, R$^{38}$, R$^{39}$, R$^{40}$, R$^{41}$, R$^{42}$, R$^{43}$ and R$^{44}$ are independently hydrogen, alkyl, substituted alkyl, aryl, substituted aryl, arylalkyl, substituted arylalkyl, cycloalkyl, substituted cycloalkyl, cycloheteroalkyl, substituted cycloheteroalkyl, heteroalkyl, substituted heteroalkyl, heteroaryl, substituted heteroaryl, heteroarylalkyl or substituted heteroarylalkyl.

"Heteroaryl" by itself or as part of another substituent, refers to a monovalent heteroaromatic radical derived by the removal of one hydrogen atom from a single atom of a heteroaromatic ring system. Typical heteroaryl groups include, but are not limited to, groups derived from acridine, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, benzodioxole and the like. In certain embodiments, the heteroaryl group is from 5-20 membered heteroaryl. In certain embodiments, the heteroaryl group is from 5-10 membered heteroaryl. In certain embodiments, heteroaryl groups are those derived from thiophene, pyrrole, benzothiophene, benzofuran, indole, pyridine, quinoline, imidazole, oxazole and pyrazine.

"Heteroarylalkyl" by itself or as part of another substituent, refers to an acyclic alkyl radical in which one of the hydrogen atoms bonded to a carbon atom, typically a terminal or sp$^3$ carbon atom, is replaced with a heteroaryl group. Where specific alkyl moieties are intended, the nomenclature heteroarylalkanyl, heteroarylalkenyl and/or heterorylalkynyl is used. In certain embodiments, the heteroarylalkyl group is a 6-30 membered heteroarylalkyl, e.g., the alkanyl, alkenyl or alkynyl moiety of the heteroarylalkyl is 1-10 membered and the heteroaryl moiety is a 5-20-membered heteroaryl. In certain embodiments, the heteroarylalkyl group is 6-20 membered heteroarylalkyl, e.g., the alkanyl, alkenyl or alkynyl moiety of the heteroarylalkyl is 1-8 membered and the heteroaryl moiety is a 5-12-membered heteroaryl.

In some embodiments, the heterocycle-containing component is an aromatic ring system. "Aromatic Ring System" by itself or as part of another substituent, refers to an unsaturated cyclic or polycyclic ring system having a conjugated π electron system. Specifically included within the definition of "aromatic ring system" are fused ring systems in which one or more of the rings are aromatic and one or more of the rings are saturated or unsaturated, such as, for example, fluorene, indane, indene, phenalene, etc. Typical aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Heteroaromatic Ring System" by itself or as part of another substituent, refers to an aromatic ring system in which one or more carbon atoms (and any associated hydrogen atoms) are independently replaced with the same or different heteroatom. Typical heteroatoms to replace the carbon atoms include, but are not limited to, N, P, O, S, Si, etc. Specifically included within the definition of "heteroaromatic ring systems" are fused ring systems in which one or more of the rings are aromatic and one or more of the rings are saturated or unsaturated, such as, for example, arsindole, benzodioxan, benzofuran, chromane, chromene, indole, indoline, xanthene, etc. Typical heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

In certain embodiments, SMART membranes of interest include a heterocyclic nitrogen containing component, such as polymers of polyvinylpyridine (PVP) and polyvinylimidazole.

SMART membranes may include PVP and a crosslinker such as a polyetheramine crosslinker. For example, a SMART membrane may include a poly(4-vinylpyridine-co-styrene) polymer backbone and a polyetheramine crosslinker.

In some instances, the poly(4-vinylpyridine-co-styrene) polymer has a styrene composition ranging from 0.01% to 50%, such as from 0.05% to 45%, such as from 0.1% to 40%, such as from 0.5% to 35%, such as from 1% to 30%, such as from 2% to 25% and including from 5% to 20%. For example, the poly(4-vinylpyridine-co-styrene) polymer may have a styrene composition of 80%.

The molecular weight of the poly(4-vinylpyridine-co-styrene) polymer may vary, in some embodiments, the poly(4-vinylpyridine-co-styrene) polymer has a molecular weight of 5 kDa or more, such as 10 kDa or more, such as 15 kDa or more, such as 20 kDa or more, such as 25 kDa or more, such as 30 kDa or more, such as 40 kDa or more, such as 50 kDa or more, such as 75 kDa or more, such as 90 kDa or more and including 100 kDa or more. For example, the molecular weight of the poly(4-vinylpyridine-co-styrene) polymer may range from 5 kDa to 150 kDa, such as from 10 kDa to 125 kDa, such as from 15 kDa to 100 kDa, such as from 20 kDa to 80 kDa, such as from 25 kDa to 75 kDa and including from 30 kDa to 60 kDa. In certain embodiments, the poly(4-vinylpyridine-co-styrene) polymer has a molecular weight of 96 kDa.

In certain embodiments, the poly(4-vinylpyridine-co-styrene) polymer includes a compound of the formula:

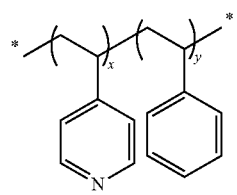

where * denotes a bond to another group, for example a PVPSty polymer of the formula above and where x and y are each positive integers. In some embodiments, x ranges from 2 to 1000, such as from 5 to 900, such as from 10 to 850, such as from 15 to 800, such as from 20 to 750, such as from 25 to 700, such as from 30 to 650, such as from 35 to 600, such as from 40 to 550 and including from 50 to 500. In these embodiments, y ranges from 2 to 1000, such as from 5 to 900, such as from 10 to 850, such as from 15 to 800, such as from 20 to 750, such as from 25 to 700, such as from 30 to 650, such as from 35 to 600, such as from 40 to 550 and including from 50 to 500. Depending on the properties of the membrane desired, the ratio of x and y may vary, ranging from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of x and y ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some instances, the ratio of x and y is 5:1. In other instances, the ratio of x and y is 4:1. In yet other instances, the ratio of x and y is 3:1. In still other instances, the ratio of x and y is 2:1. In certain instances, the ratio of x and y is 1:1. For example, in certain embodiments the ratio of y/(y+x) ranges from 0.01 to 0.5, such as from 0.05 to 0.4 and including from 0.1 to 0.35.

The molecular weight of the polyetheramine crosslinker may vary, in some embodiments, the polyetheramine crosslinker has a molecular weight of 100 daltons or more, such as 200 daltons or more, such as 300 daltons or more, such as 400 daltons or more, such as 500 daltons or more, such as 600 daltons or more, such as 700 daltons or more, such as 800 daltons or more, such as 900 daltons or more, such as 1000 daltons or more, such as 1250 daltons or more, such as 1500 daltons or more, such as 1750 daltons or more, such as 2000 daltons or more, such as 2250 daltons or more and including 2500 daltons or more. For example, the molecular weight of the polyetheramine crosslinker may range from 100 daltons to 5000 daltons, such as from 200 daltons to 4500 daltons, such as from 300 daltons to 4000 daltons, such as from 500 daltons to 3500 daltons, such as from 600 daltons to 3000 daltons, such as from 750 daltons to 2500 daltons and including from 1000 daltons to 2000 daltons. In certain embodiments, the polyetheramine crosslinker has a molecular weight of 2000 daltons.

In some embodiments, the crosslinker is a linear polyetheramine crosslinker. In some instances, the linear polyetheramine crosslinker includes a poly(propylene glycol) component and a poly(ethylene glycol) component. Depending on the properties of the membrane desired, the ratio of poly(ethylene glycol) component to poly(propylene glycol) component ranges from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of poly(ethylene glycol) component to poly(propylene glycol) component ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some instances, the ratio of poly (ethylene glycol) component to poly(propylene glycol) component is 1:5. In other instances, the ratio of poly(ethylene glycol) component to poly(propylene glycol) component is 1:4. In yet other instances, the ratio of poly(ethylene glycol) component to poly(propylene glycol) component is 1:3. In still other instances, the ratio of poly(ethylene glycol) component to poly(propylene glycol) component is 1:2. In certain instances, the ratio of poly(ethylene glycol) component to poly(propylene glycol) component is 6:29.

In some embodiments, the polyetheramine crosslinker is poly(propylene glycol)-block-poly(ethylene glycol)-block-poly(propylene glycol)-aminopropyl ether) crosslinker. For example, the polyetheramine crosslinker includes a compound of the formula:

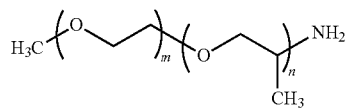

where m and n are each positive integers. In some embodiments, m ranges from 1 to 100, such as from 2 to 90, such as from 3 to 85, such as from 4 to 80, such as from 5 to 75, such as from 6 to 70, such as from 7 to 65, such as from 8 to 60, such as from 9 to 55 and including from 10 to 50. In these embodiments, n ranges from 1 to 100, such as from 2 to 90, such as from 3 to 85, such as from 4 to 80, such as from 5 to 75, such as from 6 to 70, such as from 7 to 65, such as from 8 to 60, such as from 9 to 55 and including from 10 to 50. Depending on the properties of the membrane desired, the ratio of m and n may vary, ranging from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of m and n ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some instances, the ratio of m and n is 1:5. In other instances, the ratio of m and n is 1:4. In yet other instances, the ratio of m and n is 1:3. In still other instances, the ratio of m and n is 1:2. In certain instances, the ratio of m and n is 6:29.

In some embodiments, the crosslinker is a branched polyetheramine crosslinker. In some embodiments, the branched polyetheramine crosslinker includes a poly(propylene glycol) component, a poly(ethylene glycol) component and a multi-arm branching component. Depending on the properties of the membrane desired, the ratio of poly(ethylene glycol) component to poly(propylene glycol) component ranges from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of poly(ethylene glycol) component to poly(propylene glycol) component ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some instances, the ratio of poly(ethylene glycol) component to poly(propylene glycol) component is 1:5. In other instances, the ratio of poly(ethylene glycol) component to poly(propylene glycol) component is 1:4. In yet other instances, the ratio of poly(ethylene glycol) component to poly(propylene glycol) component is 1:3. In still other instances, the ratio of poly(ethylene glycol) component to poly(propylene glycol) component is 1:2.

The multi-arm branching component may be a 3-arm branching component, a 4-arm branching component, a 5-arm branching component, a 6-arm branching component or a larger number arm branching component, such as having 7 arms or more, such as 8 arms or more, such as 9 arms or more, such as 10 arms or more and including 15 arms or more. In certain instances, the multi-arm branching component is a multi-arm epoxide, such as 3-arm epoxide or a 4-arm epoxide. Where the multi-arm branching component is a multi-arm epoxide, the multi-arm branching component may be a polyethylene glycol (PEG) multi-arm epoxide or a non-polyethylene glycol (non-PEG) multi-arm epoxide. In some embodiments, the multi-arm branching component is a non-PEG multi-arm epoxide. In other embodiments, the multi-arm branching component is a PEG multi-arm epoxide. In certain embodiments, the multi-arm branching component is a 3-arm PEG epoxide or a 4-arm PEG epoxide.

In some embodiments, the polyetheramine crosslinker includes a branched poly(propylene glycol)-block-poly(ethylene glycol)-block-poly(propylene glycol)-aminopropyl ether) crosslinker. In certain embodiments, the polyetheramine crosslinker is prepared from compounds having the formula:

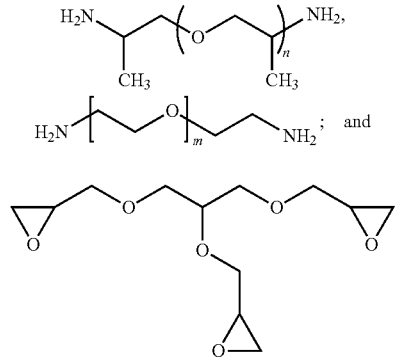

where m and n are each positive integers. In some embodiments, m ranges from 1 to 100, such as from 2 to 90, such as from 3 to 85, such as from 4 to 80, such as from 5 to 75, such as from 6 to 70, such as from 7 to 65, such as from 8 to 60, such as from 9 to 55 and including from 10 to 50. In these embodiments, n ranges from 1 to 100, such as from 2 to 90, such as from 3 to 85, such as from 4 to 80, such as from 5 to 75, such as from 6 to 70, such as from 7 to 65, such as from 8 to 60, such as from 9 to 55 and including from 10 to 50. Depending on the properties of the membrane desired, the ratio of m and n may vary, ranging from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of m and n ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some instances, the ratio of m and n is 1:5. In other instances, the ratio of m and n is 1:4. In yet other instances, the ratio of m and n is 1:3. In still other instances, the ratio of m and n is 1:2.

The ratio of poly(4-vinylpyridine-co-styrene) polymer and polyetheramine crosslinker varies, depending on the desired diffusion properties of the membrane and may range from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of poly(4-vinylpyridine-co-styrene) polymer and polyetheramine crosslinker ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some embodiments, the ratio of poly(4-vinylpyridine-co-styrene) polymer and polyetheramine crosslinker is 5:1. In other embodiments, the ratio of poly(4-vinylpyridine-co-styrene) polymer and polyetheramine crosslinker is 4:1. In yet other embodiments, the ratio of poly(4-vinylpyridine-co-styrene) polymer and polyetheramine crosslinker is 3:1. In still other embodiments the ratio of poly(4-vinylpyridine-co-styrene) polymer and polyetheramine crosslinker is 2:1.

In certain embodiments the ratio of poly(4-vinylpyridine-co-styrene) polymer and polyetheramine crosslinker is 1:1.

In some embodiments, the polyetheramine crosslinker further includes a polyethylene glycol copolymer. The molecular weight of the polyethylene glycol copolymer may be 100 daltons or more, such as 200 daltons or more, such as 300 daltons or more, such as 400 daltons or more, such as 500 daltons or more, such as 600 daltons or more, such as 700 daltons or more, such as 800 daltons or more, such as 900 daltons or more and including 1000 daltons or more. Where the subject membranes include a polyetheramine crosslinker having a polyethylene glycol copolymer, the ratio of polyetheramine and polyethylene glycol copolymer varies, ranging from 1:1 and 1:10, such as from 1:1 and 1:8, such as from 1:1 and 1:5, such as from 1:1 and 1:4 and including a ratio of polyetheramine and polyethylene glycol copolymer ranging from 1:1 and 1:2.

In other embodiments the ratio of polyetheramine and polyethylene glycol copolymer ranges from 1:1 and 10:1, such as from 1:1 and 8:1, such as from 1:1 and 5:1, such as from 1:1 and 4:1 and including a ratio of polyetheramine and polyethylene glycol copolymer ranging from 1:1 and 2:1.

In certain instances, the polyetheramine crosslinker includes a polyethylene glycol copolymer of the formula:

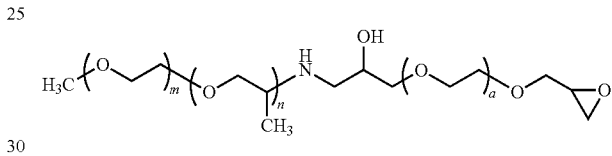

where n and m are as described above and a ranges from 1 to 100, such as from 2 to 90, such as from 3 to 85, such as from 4 to 80, such as from 5 to 75, such as from 6 to 70, such as from 7 to 65, such as from 8 to 60, such as from 9 to 55 and including from 10 to 50. In some embodiments, a is 10.

In certain embodiments, SMART membranes include poly(4-vinylpyridine-co-styrene) polymer and polyetheramine crosslinker have the following formula:

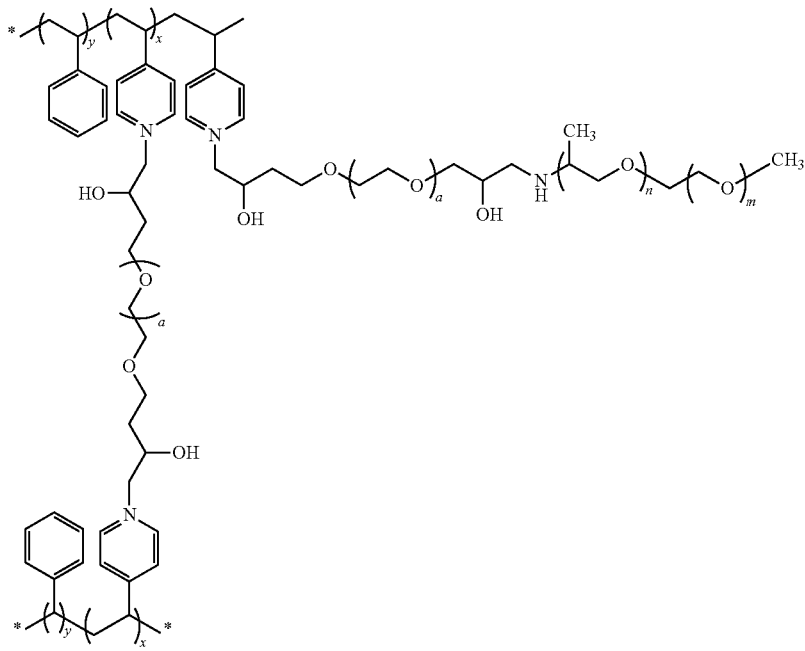

where x and y are independently positive integers ranging from 2 to 1000; m and n are independently positive integers ranging from 1 to 100 and a is a positive integer ranging from 2 to 100. In certain instances, SMART membranes of interest include poly(4-vinylpyridine-co-styrene) polymer and polyetheramine crosslinker have the following formula:

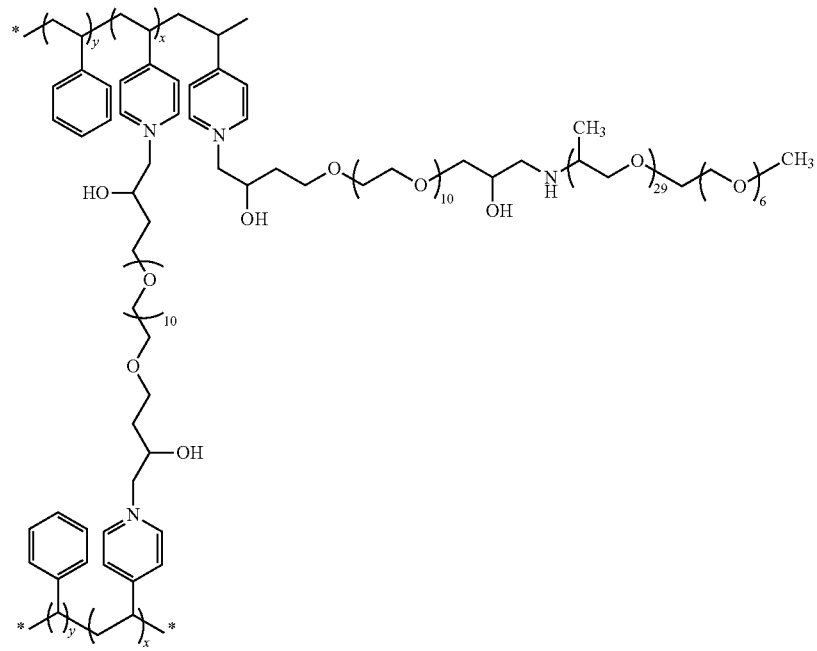

In embodiments of the present disclosure, SMART membranes having poly(4-vinylpyridine-co-styrene) polymer and polyetheramine crosslinker have a poly(4-vinylpyridine-co-styrene) polymer composition ranging from 1% to 99%, such as from 5% to 95%, such as from 10% to 90%, such as from 15% to 85%, such as from 20% to 80%, such as from 25% to 75% and including from 30% to 70%. For example, the subject membranes may have a poly(4-vinylpyridine-co-styrene) polymer composition of 20%.

The molecular weight of the SMART membranes having a poly(4-vinylpyridine-co-styrene) polymer and polyetheramine crosslinker may vary, in some embodiments, having a molecular weight of 10 kDa or more, such as 20 kDa or more, such as 25 kDa or more, such as 30 kDa or more, such as 40 kDa or more, such as 50 kDa or more, such as 75 kDa or more, such as 90 kDa or more, such as 100 kDa or more, such as 125 kDa or more and including 150 kDa or more. For example, the molecular weight of the membranes of interest having a poly(4-vinylpyridine-co-styrene) polymer and polyetheramine crosslinker may range from 5 kDa to 150 kDa, such as from 10 kDa to 125 kDa, such as from 15 kDa to 100 kDa, such as from 20 kDa to 80 kDa, such as from 25 kDa to 75 kDa and including from 30 kDa to 60 kDa. In certain embodiments, the subject membranes having a poly(4-vinylpyridine-co-styrene) polymer and polyetheramine crosslinker have a molecular weight of 98 kDa.

In certain embodiments, SMART membranes of interest include a flux limiting membrane disposed on the enzyme layer, where the flux limiting membrane includes a copolymer of poly(4-vinylpyridine-co-styrene) and polyethylene oxide-polypropylene oxide.

In SMART membranes that include a copolymer of poly(4-vinylpyridine-co-styrene) and polyethylene oxide-polypropylene oxide, the poly(4-vinylpyridine-co-styrene) component has a styrene composition ranging from 1% to 50%, such as from 2% to 45%, such as from 3% to 40%, such as from 4% to 35%, such as from 5% to 30%, such as from 6% to 25% and including from 10% to 20%. For example, the poly(4-vinylpyridine-co-styrene) component may have a styrene composition of 40%.

The molecular weight of the poly(4-vinylpyridine-co-styrene) component may vary, in some embodiments, the poly(4-vinylpyridine-co-styrene) component has a molecular weight of 5 kDa or more, such as 10 kDa or more, such as 15 kDa or more, such as 20 kDa or more, such as 25 kDa or more, such as 30 kDa or more, such as 40 kDa or more, such as 50 kDa or more, such as 75 kDa or more, such as 90 kDa or more and including 100 kDa or more. For example, the molecular weight of the poly(4-vinylpyridine-co-styrene) component may range from 5 kDa to 150 kDa, such as from 10 kDa to 125 kDa, such as from 15 kDa to 100 kDa, such as from 20 kDa to 80 kDa, such as from 25 kDa to 75 kDa and including from 30 kDa to 60 kDa. In certain embodiments, the poly(4-vinylpyridine-co-styrene) component has a molecular weight of 96 kDa.

In certain embodiments, the poly(4-vinylpyridine-co-styrene) component includes a compound of the formula:

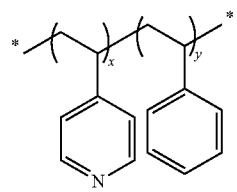

where * denotes a bond to another group, for example a polyethylene oxide-polypropylene oxide copolymer as described below and x and y are each positive integers. In some embodiments, x ranges from 2 to 1000, such as from 5 to 900, such as from 10 to 850, such as from 15 to 800, such as from 20 to 750, such as from 25 to 700, such as from 30 to 650, such as from 35 to 600, such as from 40 to 550 and including from 50 to 500. In these embodiments, y ranges from 2 to 1000, such as from 5 to 900, such as from 10 to 850, such as from 15 to 800, such as from 20 to 750, such as from 25 to 700, such as from 30 to 650, such as from 35 to 600, such as from 40 to 550 and including from 50 to 500. Depending on the properties of the membrane desired, the ratio of x and y may vary, ranging from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of x and y ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some instances, the ratio of x and y is 5:1. In other instances, the ratio of x and y is 4:1. In yet other instances, the ratio of x and y is 3:1. In still other instances, the ratio of x and y is 2:1. In certain instances, the ratio of x and y is 1:1.

In some embodiments, the polyethylene oxide-polypropylene oxide component includes a PEO-PPO-PEO polymer. In other embodiments, the polyethylene oxide-polypropylene oxide component includes a PPO-PEO-PPO polymer. The molecular weight of the polyethylene oxide-polypropylene oxide component may vary, in some embodiments, the polyethylene oxide-polypropylene oxide component has a molecular weight of 100 daltons or more, such as 200 daltons or more, such as 300 daltons or more, such as 400 daltons or more, such as 500 daltons or more, such as 600 daltons or more, such as 700 daltons or more, such as 800 daltons or more, such as 900 daltons or more, such as 1000 daltons or more, such as 1250 daltons or more, such as 1500 daltons or more, such as 1750 daltons or more, such as 2000 daltons or more, such as 2250 daltons or more and including 2500 daltons or more. For example, the molecular weight of the polyethylene oxide-polypropylene oxide component may range from 100 daltons to 5000 daltons, such as from 200 daltons to 4500 daltons, such as from 300 daltons to 4000 daltons, such as from 500 daltons to 3500 daltons, such as from 600 daltons to 3000 daltons, such as from 750 daltons to 2500 daltons and including from 1000 daltons to 2000 daltons. In certain embodiments, the polyethylene oxide-polypropylene oxide component has a molecular weight of 2000 daltons.

In some embodiments, the polyethylene oxide-polypropylene oxide component includes a compound of the formula:

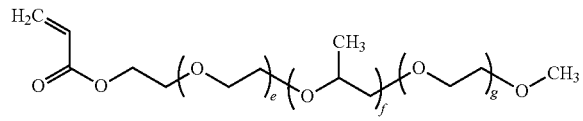

where e, f and g are independently positive integers ranging from 1 to 100. For example, in embodiments, e ranges from 1 to 100, such as from 2 to 90, such as from 3 to 85, such as from 4 to 80, such as from 5 to 75, such as from 6 to 70 and including from 5 to 20, such as 7. In these embodiments, f ranges from 1 to 100, such as from 2 to 90, such as from 3 to 85, such as from 4 to 80, such as from 5 to 75, such as from 6 to 70, such as from 10 to 50, such as from 15 to 40 and including from 20 to 30, such as 29. Also, g ranges from 1 to 100, such as from 2 to 90, such as from 3 to 85, such as from 4 to 80, such as from 5 to 75, such as from 6 to 70 and including from 10 to 20, such as 14. Depending on the properties of the membrane desired, the ratio of e and g may vary, ranging from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In certain embodiments, the ratio of e and g is 1:2. The ratio of e and f may also vary, ranging from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5 and including from 1:1 and 1:4. In certain embodiments, the ratio of e and f is 1:4. The ratio of f and g may also vary, ranging from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1 and including from 1:1 and 3:1. In certain embodiments, the ratio of f and g is 2:1. In certain instances, the ratio of e and f and g is 7:29:14.

The ratio of poly(4-vinylpyridine-co-styrene) component and polyethylene oxide-polypropylene oxide component varies, depending on the desired diffusion properties of the membrane and may range from 1:1 and 1:100, such as from 1:1 and 1:95, such as from 1:1 and 1:80, such as from 1:1 and 1:75, such as from 1:1 and 1:50, such as from 1:1 and 1:25, such as from 1:1 and 1:10, such as from 1:1 and 1:5, such as from 1:1 and 1:3 and including from 1:1 and 1:2. In other embodiments, the ratio of poly(4-vinylpyridine-co-styrene) component and polyethylene oxide-polypropylene oxide component ranges from 1:1 and 100:1, such as from 1:1 and 95:1, such as from 1:1 and 80:1, such as from 1:1 and 75:1, such as from 1:1 and 50:1, such as from 1:1 and 25:1, such as from 1:1 and 10:1, such as from 1:1 and 5:1, such as from 1:1 and 3:1 and including from 1:1 and 2:1. In some embodiments, the ratio of poly(4-vinylpyridine-co-styrene) component and polyethylene oxide-polypropylene oxide component is 5:1. In other embodiments, the ratio of poly(4-vinylpyridine-co-styrene) component and polyethylene oxide-polypropylene oxide component is 4:1. In yet other embodiments, the ratio of poly(4-vinylpyridine-co-styrene) component and polyethylene oxide-polypropylene oxide component is 3:1. In still other embodiments the ratio of poly(4-vinylpyridine-co-styrene) component and polyethylene oxide-polypropylene oxide component is 2:1. In certain embodiments the ratio of poly(4-vinylpyridine-co-styrene) component and polyethylene oxide-polypropylene oxide component is 1:1.

In certain embodiments, SMART membranes that include a copolymer of poly(4-vinylpyridine-co-styrene) and polyethylene oxide-polypropylene oxide have the following formula:

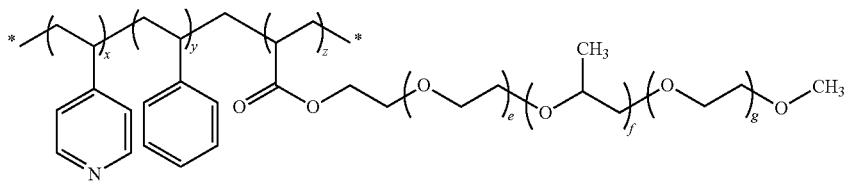

where x, y and z are independently positive integers ranging from 2 to 1000 and e, f and g are independently positive integers ranging from 1 to 100. In certain instances, SMART membranes include a copolymer poly(4-vinylpyridine-co-styrene) and polyethylene oxide-polypropylene oxide having the following formula:

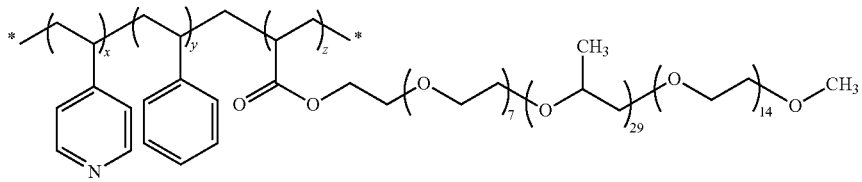

The molecular weight of subject flux limiting membranes having a copolymer poly(4-vinylpyridine-co-styrene) polymer and polyethylene oxide-polypropylene oxide may vary, in some embodiments, having a molecular weight of 10 kDa or more, such as 20 kDa or more, such as 25 kDa or more, such as 30 kDa or more, such as 40 kDa or more, such as 50 kDa or more, such as 75 kDa or more, such as 90 kDa or more, such as 100 kDa or more, such as 125 kDa or more and including 150 kDa or more. For example, the molecular weight of the membranes of interest having a copolymer poly(4-vinylpyridine-co-styrene) polymer and polyethylene oxide-polypropylene oxide may range from 5 kDa to 150 kDa, such as from 10 kDa to 125 kDa, such as from 15 kDa to 100 kDa, such as from 20 kDa to 80 kDa, such as from 25 kDa to 75 kDa and including from 30 kDa to 60 kDa. In certain embodiments, the subject membranes having a copolymer of poly(4-vinylpyridine-co-styrene) polymer and polyethylene oxide-polypropylene oxide have a molecular weight of 100 kDa.

Analyte Sensors that Include Low Temperature Sensitivity Membranes

Also disclosed are sensors that include one or more SMART membranes. In some embodiments, SMART sensors are in vivo wholly positioned electrochemical analyte sensors, and in other embodiments the SMART sensors are transcutaneously positioned electrochemical analyte sensors configured for in vivo positioning in a subject. For example, at least a portion of a SMART in vivo sensor may be positioned in the subcutaneous tissue or dermal tissue for testing analyte concentrations in interstitial fluid.

Aspects of the present disclosure also include analyte sensors (e.g., electrochemical sensors) employing a working electrode and a reference electrode, where the working electrode includes an enzyme layer positioned proximate to a working electrode and one or more of the subject SMART membranes proximate to (e.g., entirely covering, on top of and/or in contact with) the enzyme layer. These analyte sensors are SMART sensors in that they are temperature independent as disclosed herein.

In some embodiments, the SMART membrane is disposed on top of and bonded to the enzyme layer. By "bonded" is meant any type of an interaction between atoms or molecules that allows chemical compounds to form associations with each other, such as, but not limited to, covalent bonds, ionic bonds, dipole-dipole interactions, hydrogen bonds, London dispersion forces, and the like. In some instances, the SMART sensor includes an enzyme layer and a SMART membrane disposed on and covalently bonded to the enzyme layer. For example, in situ polymerization of the SMART membrane can form crosslinks between the polymers of the SMART membrane and the polymers in the enzyme layer. In certain embodiments, crosslinking of the SMART membrane to the enzyme layer facilitates a reduction in the occurrence of delamination of the SMART membrane from the enzyme layer.

Analytes that can be monitored using the subject analyte sensors are described herein. In certain embodiments, the analyte sensors of the present disclosure are in vivo glucose sensors. The disclosed analyte sensors may include an analyte-responsive enzyme and a redox mediator. For example, a glucose oxidase (GOD) or glucose dehydrogenase (GDH) can be used when the analyte is glucose. A lactate oxidase can be used when the analyte is lactate. Hydroxybutyrate dehydrogenase can be used when the analyte is a ketone. In order to facilitate electrochemical reaction, the analyte sensor may further include an enzyme co-factor. For example, suitable cofactors include pyrroloquinoline quinone (PQQ), and flavin adenine dinucleotide (FAD). Additional analyte-responsive enzymes and cofactors which may be suitable with the analyte sensors disclosed herein are described in U.S. Pat. No. 6,736,957, the disclosure of which is herein incorporated by reference. In certain embodiments, the redox species is a transition metal compound or complex. The transition metal compounds or complexes may be osmium, ruthenium, iron, and cobalt compounds or complexes. Suitable redox mediators and methods for producing them are described in U.S. Pat. Nos. 5,262,035; 5,264,104; 5,320,725; 5,356,786; 6,592,745; and 7,501,053, the disclosure of each of which is herein incorporated by reference. Examples of suitable in vivo electrochemical analyte sensors and methods for making them which may include one or more of membranes which exhibit low temperature sensitivity as described herein include, but are not limited to, those described in U.S. Pat. Nos. 6,175,752, 6,134,461, 6,579,690, 6,605,200, 6,605,201, 5,356,786, 6,560,471, 5,262,035, 6,881,551, 6,121,009, 5,262,305, 6,600,997, 6,514,718, 7,299,082, 7,811,231, 8,106,780, 8,601,465, and; U.S. Patent Application Publication Nos. 2010/0198034, 2010/0324392, 2010/0326842, 2010/0213057, 2011/0120865, 2011/0213225, 2011/0256024, 2011/0257495, 2012/0157801, 2012/0157801, 2012/0245447, 2012/0323098, the disclosures of each of which are incorporated herein by reference in their entirety.

In certain instances as the temperature changes, SMART in vivo sensors that include one or more of the subject SMART membranes have a sensitivity of 0.1 nA/mM or more, or 0.5 nA/mM or more, such as 1 nA/mM or more, including 1.5 nA/mM or more, for instance 2 nA/mM or more, or 2.5 nA/mM or more, or 5 nA/mM or more, or 7.5 nA/mM or more, or 10 nA/mM or more, or 12.5 nA/mM or more, or 15 nA/mM or more. In some embodiments, SMART sensors retain initial sensitivity for an extended period of time. In some instances, even when exposed to changes in temperature, the sensor retains a sensitivity that is 85-100%, such as 90 to 98% of the initial sensitivity after 1 day or more, such as 2 days or more, 3 days or more, 4 days or more, 5 days or more, 6 days or more, 7 days or more, 10 days or more, 14 days or more, 1 month or more, 2 months or more, 4 months or more, 6 months or more, 9 months or more, or 1 year or more. A Smart sensor may exhibit increasing sensitivity over its in vivo use period, and its accuracy may also increase over time, e.g., as measured by MARD, or the like, even over changes in temperature to which it is exposed.

A variety of approaches may be employed to determine the concentration of the analyte. In certain aspects, an electrochemical analyte concentration monitoring approach is used. For example, monitoring the concentration of the analyte using the sensor signal may be performed by coulometric, amperometric, voltammetric, potentiometric, or any other convenient electrochemical detection technique.

When analyte is monitored, its presence and/or concentration and/or rate of change and/or trend, among others, may be displayed, stored, and/or otherwise processed. As demonstrated herein, the devices, systems and methods disclosed herein are useful when there is at least suspicion of exposure to or potential or exposure to changing temperatures or temperatures that are at least suspected of being detrimental to the analyte sensor. Analytes and fluids for analyte monitoring are described elsewhere herein.

Briefly, methods for using a SMART in vivo analyte sensor may include positioning at least a portion of the SMART sensor beneath a skin surface of a user, for example, into a site such that interstitial fluid, dermal fluid or blood comes into contact with the sensor (e.g., subcutaneous tissue, dermal space, or blood vessel). The SMART sensor is operated to electrolyze an analyte (e.g., glucose) in the biological fluid such that a current is generated between the working electrode and the counter electrode. A value for the current associated with the working electrode is determined. If multiple working electrodes are used, current values from each of the working electrodes may be determined. A microprocessor may be used to collect these periodically determined current values or to further process these values. During these methods, the sensor may be exposed to changes in temperature and/or a temperature that is detrimental to the analyte monitoring process. Accordingly, temperature insensitive analyte monitoring methods include exposing an in vivo positioned sensor to changes in temperature and/or a temperature that is detrimental to the analyte monitoring process, and maintaining temperature insensitive rate of analyte permeation through the membrane of the sensor to generate analyte results that are temperature insensitive.

For example, in some embodiments, the method includes positioning at least a portion of a SMART analyte sensor into the skin of the subject and determining a level of glucose over a period of time from signals generated by the SMART analyte sensor. In certain embodiments, the method further includes attaching a SMART analyte sensor electronics unit to the skin of the patient, coupling one or more conductive contacts of the SMART sensor analyte sensor electronics unit to one or more electrical contacts of the electronics unit either before or after attaching the electronic unit to the skin, collecting temperature insensitive analyte information from the in vivo sensor/electronic unit, and communicating the temperature insensitive analyte collected data from the analyte sensor control unit to a receiver unit. In some embodiments, the temperature insensitive analyte data is transferred automatically according to a predetermined or random interval, such as such as every 0.01 minutes, every 0.05 minutes, every 0.1 minutes, every 0.5 minutes, every 1 minute, every 5 minutes, every 10 minutes, every 30 minutes, every 60 minutes or some other interval, such as every 1 hour, every 2 hours, every 3 hours, every 6 hours, every 12 hours, every 24 hours, such as every 1 day, every 2 days, every 3 days, every 7 days, etc.

In yet other embodiments, the temperature insensitive analyte data is transferred by initiation of a request for the collected data, such as with a device in communication (e.g., wirelessly or through a wire) with the SMART analyte sensor electronics unit. Embodiments include using one or more radiofrequency protocols. Some embodiments use Bluetooth, RFID, etc., to transfer temperature insensitive analyte data from the on-body electronics unit to a reader. For example, the SMART sensor data may be communicated from the sensor electronics to the reader monitoring device using RFID technology (active, passive or semi passive), and communicated whenever the sensor electronics are brought into communication range of the reader device. For example, the in vivo positioned sensor may collect sensor data in memory until the reader device is brought into communication range of the sensor electronics unit—e.g., by the user. In some instances, the in vivo positioned sensor/electronics is detected by the analyte monitoring device, the device establishes communication with the sensor electronics and uploads the sensor data that has been collected since the last transfer of sensor data. In yet other embodiments, transfers of sensor data may be initiated when brought into communication range, and then continued on an automated basis according to a predetermined schedule if continued to remain in communication range. Additional information regarding RFID tags and readers is provided, for example, in U.S. Patent Application Publication No. 2010/0063374, the disclosure of which is incorporated by reference herein.

A reader unit may include an in vitro analyte meter, a personal computer, a portable computer including a laptop or a handheld device (e.g., a personal digital assistant (PDA), a tablet computer, a telephone including a mobile phone (e.g., a multimedia and Internet-enabled mobile phone including a smartphone, or similar phone), a digital mP3 player (a pager, and the like), a drug delivery device (e.g., an infusion device), or devices including combinations thereof, each of which may be configured for data communication with the data processing unit via a wired or a wireless connection.

EXPERIMENTAL

The following examples are put forth so as to provide those of ordinary skill in the art with a complete disclosure and description of how to make and use the embodiments of the invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

In Vivo Glucose Sensors Having SMART Membranes of Poly(4-vinylpyridine-co-styrene) Polymer and a Polyetheramine Crosslinker Experiments were performed to test SMART membrane formulations that included a poly(4-vinylpyridine-co-styrene) polymer and a polyetheramine crosslinker. The SMART membrane was prepared and tested as follows.

SMART Membrane Formulation

For the polyetheramine crosslinker solution, a 400 mg/mL solution of a poly(propylene glycol)-block-poly(ethylene glycol)-block-poly(propylene glycol)-aminopropyl ether) crosslinker having a ratio of poly(ethylene glycol) to poly(propylene glycol) of 6 to 29 in ethanol/Hepes (80/20) and 200 mg/mL PEG 400 (polyethylene glycol) (400) diglycidyl ether in ethanol/Hepes (80/20) were stirred at room temperature for 2 days. A schematic of the reaction is shown in Scheme 1.

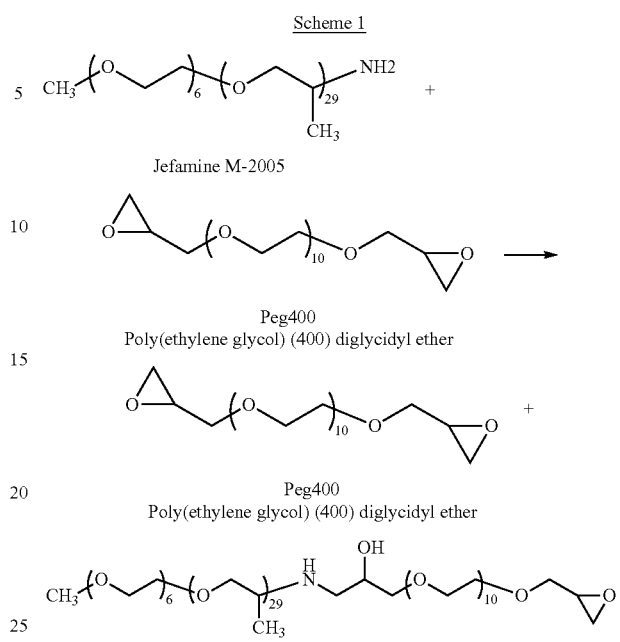

Scheme 1

Poly(4-vinylpyridine-co-styrene) (20%) having a molecular weight of 96 kDa was prepared at a concentration of 150 mg/mL in ethanol. 2 mL of the poly(4-vinylpyridine-co-styrene) solution was added to 0.5 mL Hepes to produce a 2.5 mL ethanol/Hepes (80/20) solution. The 2.5 mL ethanol/Hepes (80/20) solution of poly(4-vinylpyridine-co-styrene) solution was combined with the 0.5 mL of the polyetheramine crosslinker solution and stirred for 30 minutes. The SMART membrane formed in this reaction includes a compound of formula:

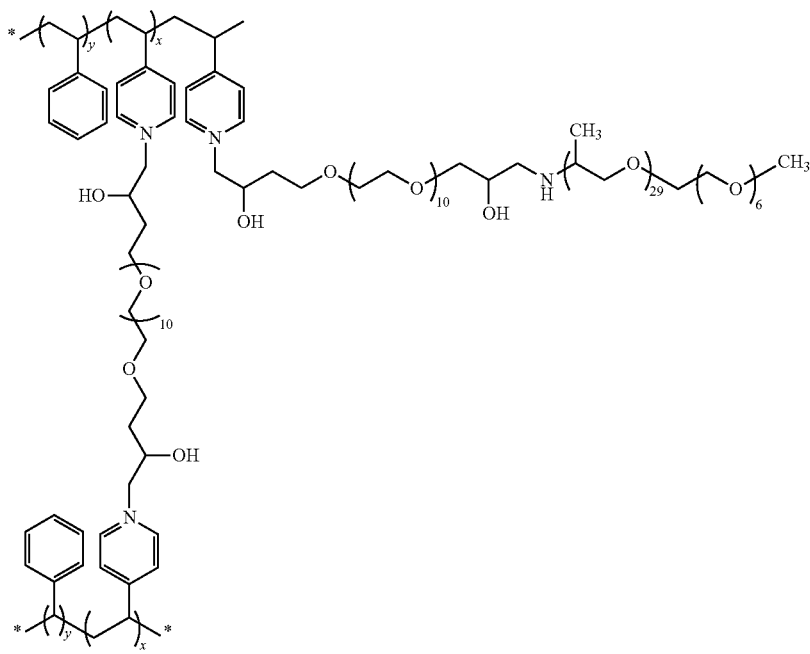

SMART In Vivo Glucose Sensors

In vivo glucose sensors having a working electrode that includes: 1) glucose oxidase (GOX) or 2) glucose dehydrogenase/flavin adenine dinucleotide (GDH/FAD) in the enzyme layer were coated with the SMART membrane described above of ethanol/Hepes solution of poly(4-vinylpyridine-co-styrene) polymer and a polyetheramine crosslinker. The SMART membrane formulation was coated onto the enzyme areas of the in vivo glucose sensors by dipping the respective working electrodes into the ethanol/Hepes solution of poly(4-vinylpyridine-co-styrene) polymer polyetheramine crosslinker at a rate of 50 mm/sec producing a SMART membrane having a thickness of 30 μm. A control sensor was prepared by coating a poly(4-vinylpyridine-co-styrene) polymer membrane onto a working electrode having a GOX enzyme layer. Examples of poly(4-vinylpyridine-co-styrene) polymer membranes used as controls include those described in U.S. Pat. No. 6,932,894, the disclosure of which is herein incorporated by reference.

Testing Method

The in vivo glucose sensors were tested in 0.1 M phosphate buffer (PBS) buffer containing 10 mM glucose at temperatures ranging from 27° C. to 42° C. The temperature was controlled by a circulated water system with a digital temperature controller.

ited significantly less sensitivity to changes in temperature as compared to the in vivo glucose sensor employing the control membrane. FIG. 1 shows that the glucose sensor having GDH/FAD with the SMART membrane exhibited a change of normalized sensitivity of sensor signal of less than 0.5% per ° C. over the tested temperature range. The glucose sensor having GOX with the SMART membrane also showed little change in normalized sensitivity of sensor signal in response to the changes in temperature when tested in both 2% oxygen and in air. In 2% oxygen, the glucose sensor having a sensor layer of GOX coated with the SMART membrane exhibited a change in normalized sensitivity of sensor signal of less than 2.3% per ° C. over the tested temperature range. In air, the glucose sensor having a sensor layer of GOX coated with the SMART membrane exhibited a change in normalized sensitivity of sensor signal of less than 5.3% per ° C. over the tested temperature range. In contrast, control sensors having GOX with the poly(4-vinylpyridine-co-styrene) control membrane exhibited changes in normalized sensitivity of sensor signal of as high as 8.9% per ° C. over the same tested temperature range (27° C. to 42° C.). Table 1 below summarizes the normalized sensitivity of sensor signals depicted in FIG. 1.

TABLE 1

| Sensor/ Membrane Type | Normalized Current at Different Temperatures (nA, 5 mM glucose) | | | | % Increase per ° C. under Air | | |
|---|---|---|---|---|---|---|---|
| | 27° C. | 32° C. | 37° C. | 42° C. | 27° C. to 32° C. | 32° C. to 37° C. | 37° C. to 42° C. |
| GDH/FAD SMART membrane (Air) | 1 | 0.960656 | 1.048349 | 1.065546 | −0.8% | 1.8% | 0.3% |
| GOX/ SMART membrane (Air) | 1 | 1.191016 | 1.5383 | 1.621716 | 3.6% | 5.3% | 1.1% |
| GOX/ SMART membrane (2% O$_2$) | 1 | 1.090116 | 1.223497 | 1.278947 | 1.7% | 2.3% | 0.9% |
| GOX/ Control membrane (Air) | 1 | 1.52615 | 2.241726 | 3.175175 | 8.9% | 7.9% | 7.2% |

FIG. 1 shows normalized sensitivity of sensor signal at temperatures ranging from 27° C. to 42° C. comparing the in vivo glucose sensors having SMART membranes to the control glucose sensor. As shown in FIG. 1, the in vivo glucose sensors that included a SMART membrane exhib- The percent increase per degree in normalized sensitivity of sensor signal of in vivo glucose sensors that included SMART membranes of a poly(4-vinylpyridine-co-styrene) polymer and a polyetheramine crosslinker under air is summarized in Table 2.

TABLE 2

| Sensor/ Membrane Type | % Increase per ° C. under Air | | | | | | | | | | | | | |
|---|---|---|---|---|---|---|---|---|---|---|---|---|---|---|
| | 27° C. to 32° C. | | 32° C. to 37° C. | | 37° C. to 42° C. | | 42° C. to 37° C. | | 37° C. to 32° C. | | 32° C. to 27° C. | | 27° C. to 34° C. | |
| | individual | average | individual | average | individual | average | individual | average | individual | average | individual | average | individual | average |
| GOX/SMART membrane Sensor 1 | 0.0% | −0.1% | 0.0% | 0.2% | 0.9% | 0.8% | −1.3% | −1.0% | −0.4% | −0.6% | 0.5% | 0.3% | 0.0% | 0.0% |

TABLE 2-continued

| | % Increase per ° C. under Air | | | | | | | | | | | | | |
|---|---|---|---|---|---|---|---|---|---|---|---|---|---|---|
| | 27° C. to 32° C. | | 32° C. to 37° C. | | 37° C. to 42° C. | | 42° C. to 37° C. | | 37° C. to 32° C. | | 32° C. to 27° C. | | 27° C. to 34° C. | |
| Sensor/ Membrane Type | individual | average | individual | average | individual | average | individual | average | individual | average | individual | average | individual | average |
| GOX/SMART membrane Sensor 2 | 0.0% | | 0.0% | | 1.5% | | −1.4% | | −0.5% | | 0.5% | | 0.0% | |
| GOX/SMART membrane Sensor 3 | 0.0% | | 0.0% | | 0.4% | | −0.4% | | −0.9% | | 0.0% | | 0.0% | |
| GOX/SMART membrane Sensor 4 | −0.4% | | 0.4% | | 0.4% | | −0.7% | | −0.4% | | 0.4% | | 0.0% | |
| GDH/FAD SMART membrane Sensor 1 | −0.4% | 0.4% | −0.4% | −0.2% | 0.7% | 0.4% | −0.7% | −0.6% | 0.0% | −0.2% | 0.7% | 0.5% | −0.5% | −0.3% |
| GDH/FAD SMART membrane Sensor 2 | −0.3% | | 0.0% | | 0.3% | | −0.3% | | −0.7% | | 0.4% | | 0.0% | |
| GDH/FAD SMART membrane Sensor 3 | −0.3% | | −0.7% | | 0.3% | | −0.7% | | 0.3% | | 0.3% | | −0.5% | |
| GDH/FAD SMART membrane Sensor 4 | −0.4% | | 0.4% | | 0.4% | | −0.8% | | −0.4% | | 0.4% | | −0.3% | |
| GOX/Control Membrane Sensor 1 | 6.1% | 8.6% | 8.0% | 7.8% | 6.7% | 7.0% | −6.2% | −6.4% | −5.9% | −7.0% | −7.3% | −7.8% | 7.6% | 8.0% |
| GOX/Control Membrane Sensor 2 | 9.0% | | 7.6% | | 7.0% | | −6.6% | | −7.1% | | −7.6% | | 7.8% | |
| GOX Control Membrane Sensor 3 | 8.5% | | 8.2% | | 7.0% | | −6.5% | | −6.9% | | −8.5% | | 8.6% | |
| GOX/Control Membrane Sensor 4 | 8.8% | | 7.4% | | 7.3% | | −6.4% | | −7.3% | | −8.0% | | 8.2% | |

Figure 2:
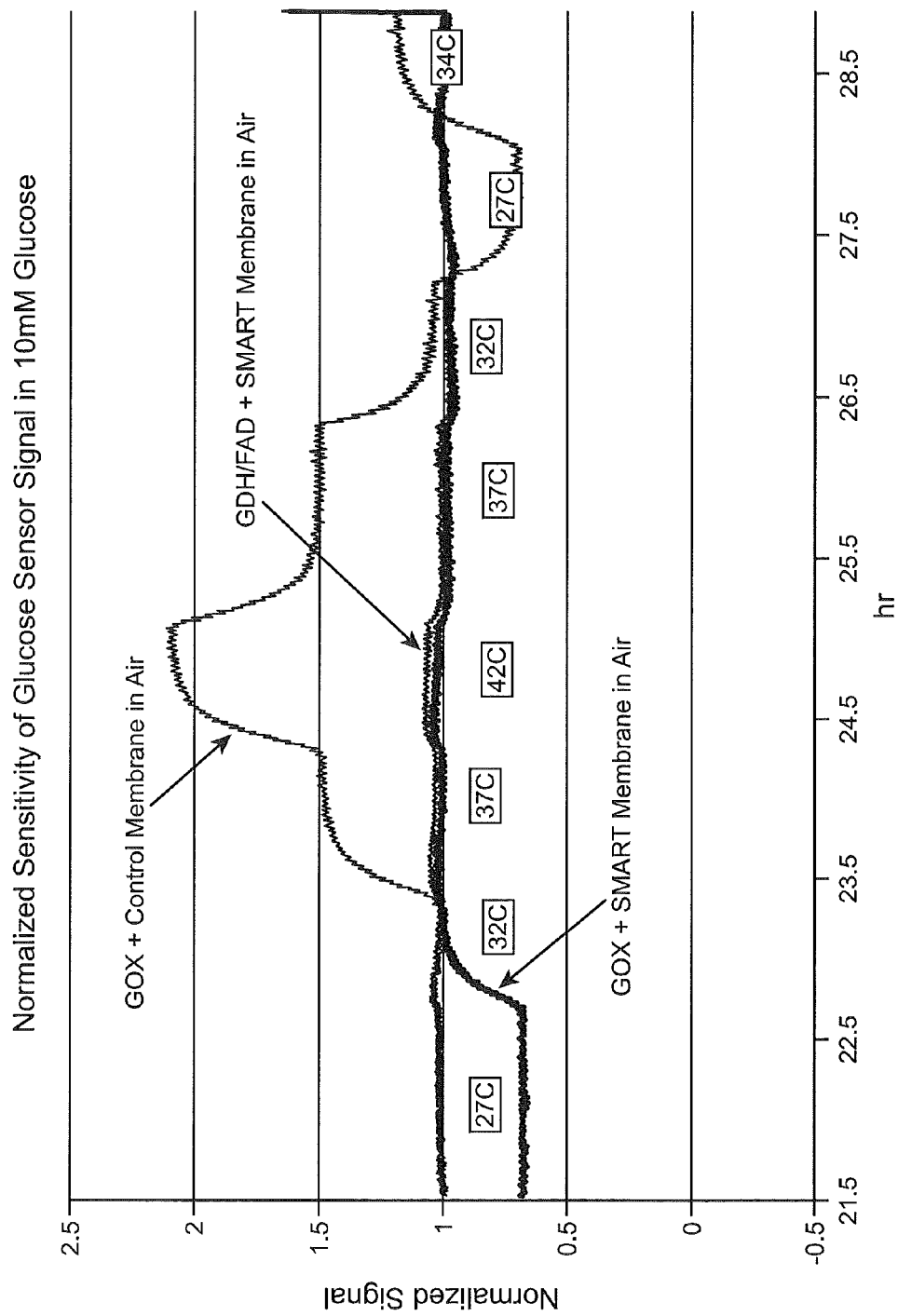
FIG. 2 shows a graph of normalized sensitivity of signal sensor over time at temperatures ranging from 27° C. to 42° C. comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane.

FIG. 2 depicts the change over time in normalized sensitivity of sensor signal at temperatures ranging from 27° C. to 42° C. for the SMART in vivo glucose sensors and the control glucose sensor. FIG. 2 demonstrates that the SMART glucose sensors (both with GDH/FAD enzyme layer and GOX enzyme layer) coated with SMART membranes exhibited little to no change in normalized sensitivity of sensor signal over the range of temperatures tested, whereas control sensors exhibited much larger temperature sensitivity, in particular at temperatures between 37° C. and 42° C., that have the potential to negatively impact the glucose concentration determination.

Figure 3:
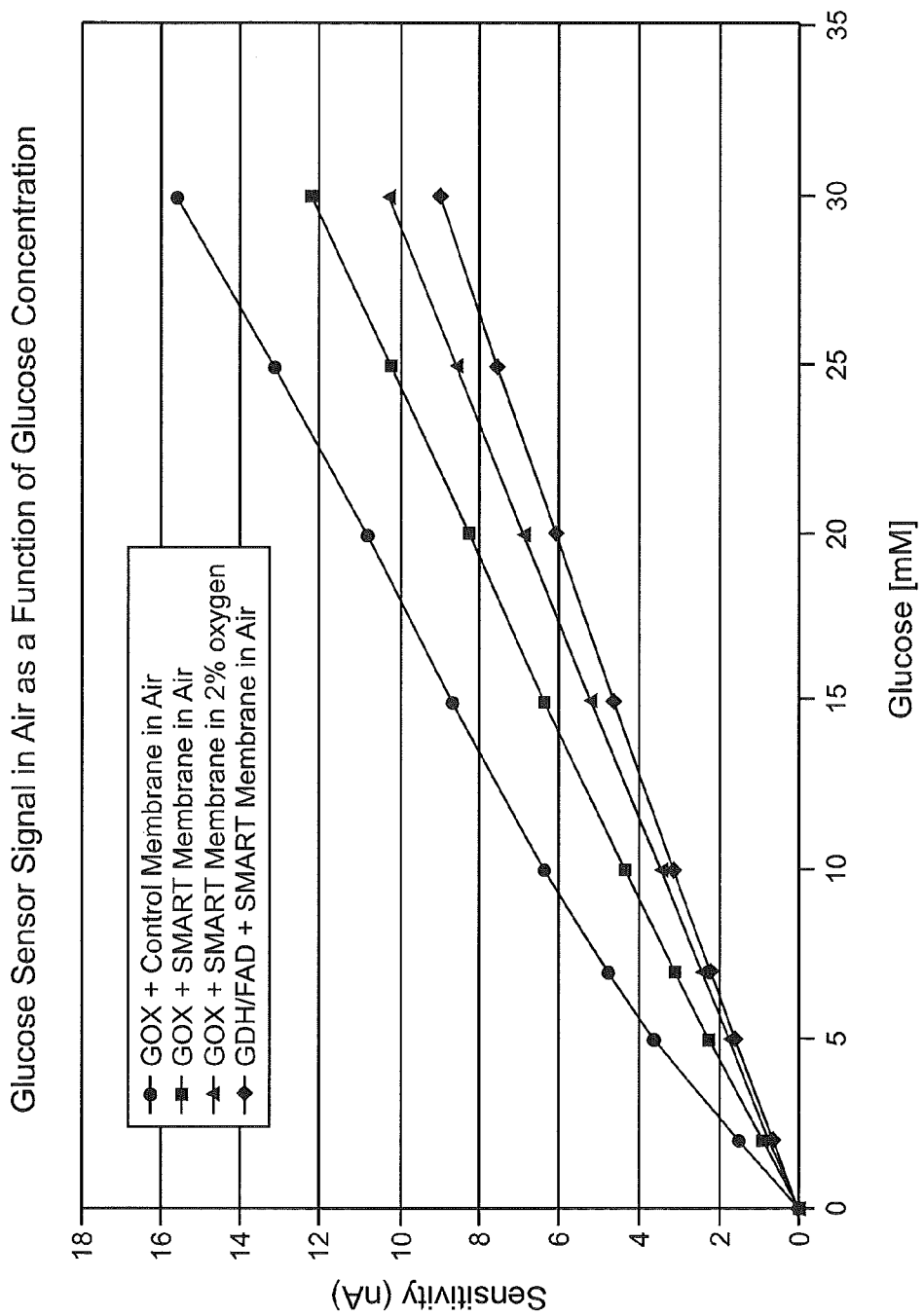
FIG. 3 shows a graph of sensor signal (in nA) as a function of glucose concentration (0 mM to 30 mM in phosphate buffer) comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane.

The in vivo glucose sensors having SMART membranes also exhibited good stability and linearity as a function of glucose concentration ranging from 0 mM to 30 mM. FIG. 3 depicts sensor signal (in nA) of the in vivo glucose sensors employing SMART membranes and the control glucose sensor in PBS having a glucose concentration ranging from 0 mM to 30 mM. As shown in FIG. 3, the sensor signals for all of the in vivo glucose sensors employing the SMART membranes were linear over the tested concentration range.

Figure 4:
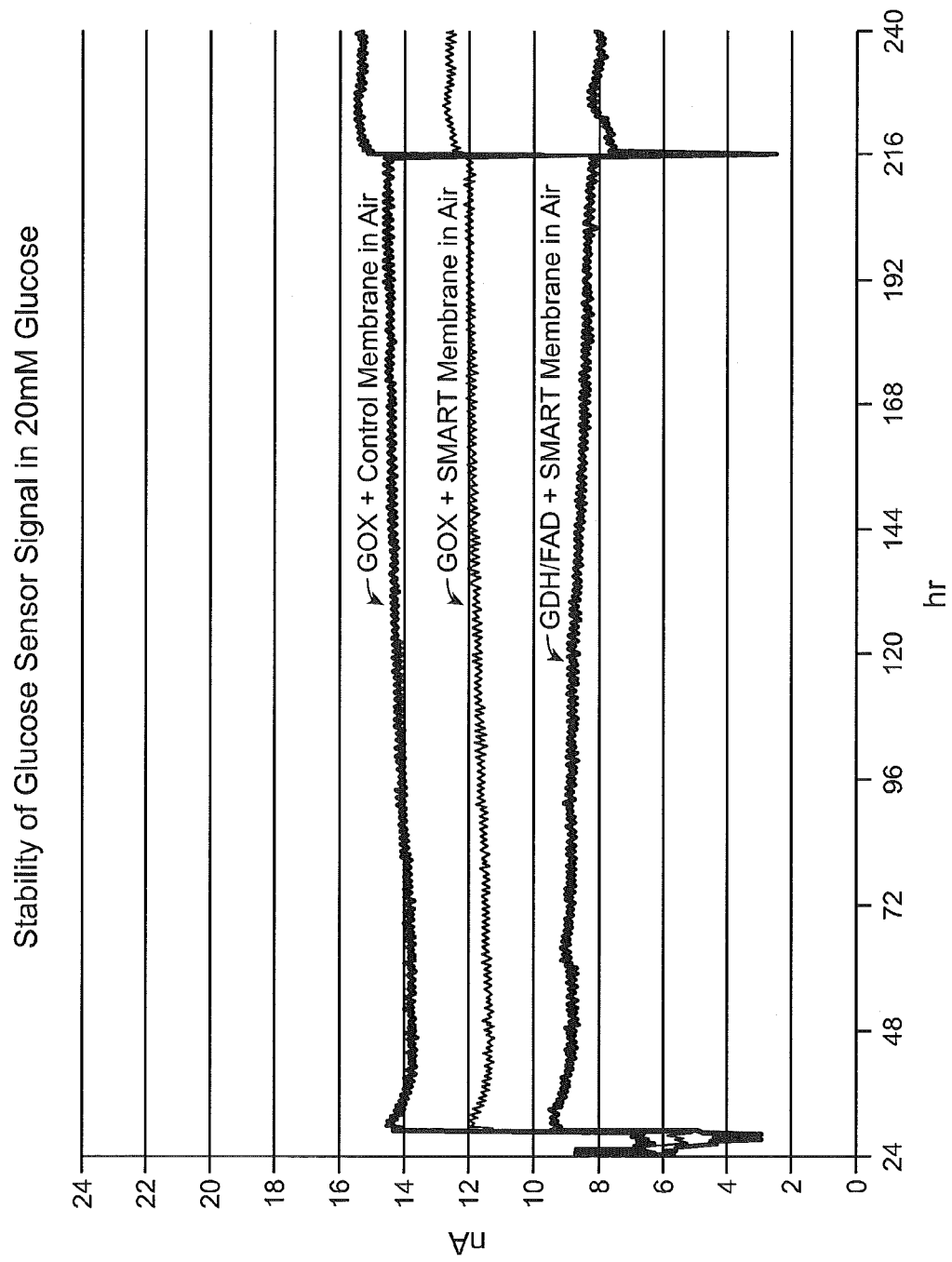
FIG. 4 shows a graph of sensor signal (in nA) stability over time at 34° C. in a solution having a glucose concentration of 20 mM comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane.

The in vivo glucose sensors having SMART membranes showed good stability at 34° C. for over 200 hours of continuous use. Sensor signal was monitored by placing the sensor in a beaker of 20 mM glucose in phosphate buffer while stirring for a period of 240 hours. FIG. 4 compares the sensor signal as a function of time (in hours) of glucose sensors having SMART membranes to the control sensor in the 20 mM glucose solution. As shown in FIG. 4, sensor signal for in vivo glucose sensors having SMART membranes were stable for well over 200 continuous hours. Sensor signal stability measured at the end of the study (after 240 hours) was found to be the same as at the commencement of the study.

Example 2

In Vivo Glucose Sensors Having SMART Membranes of Poly(4-vinylpyridine-co-styrene) Polymer and a Polyetheramine Crosslinker Experiments were performed to test SMART membrane formulations that included a poly(4-vinylpyridine-co-styrene) polymer and a polyetheramine crosslinker. The membrane formulation was prepared and tested as follows.

Membrane Formulation

For the polyetheramine crosslinker solution, a 400 mg/mL solution of a poly(propylene glycol)-block-poly(ethylene glycol)-block-poly(propylene glycol)-aminopropyl ether) crosslinker having a ratio of poly(ethylene glycol) to poly(propylene glycol) of 6 to 29 in ethanol/Hepes (80/20) and 200 mg/mL PEG 400 (polyethylene glycol) (400) diglycidyl ether in ethanol/Hepes (80/20) were stirred at room temperature for 8 days and at 55° C. for an additional 3 days until reaction completion. A schematic of the reaction is shown in Scheme 1 above.

Poly(4-vinylpyridine-co-styrene) (20%) having a molecular weight of 96 kDa was prepared at a concentration of 150 mg/mL in ethanol. 2 mL of the poly(4-vinylpyridine-co-styrene) solution was added to 0.5 mL of the polyetheramine crosslinker solution and stirred for 2 days at 55° C. and drop wise the solution was added to 100 mL deionized water. The precipitate was collected and washed with deionized water and dried under vacuum. A schematic of this reaction is shown in Scheme 2:

Scheme 2

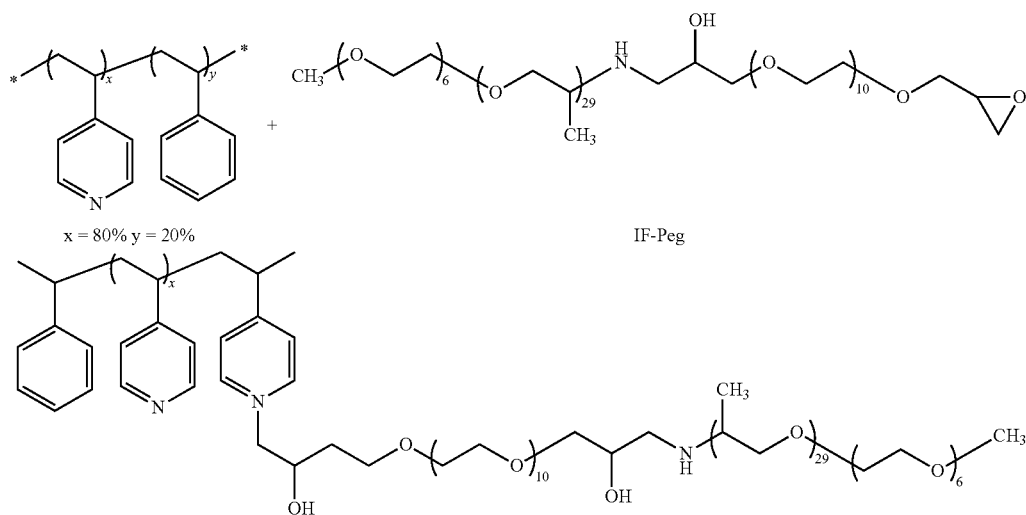

Mixing the formed polymer with PEG 400 (polyethylene glycol) (400) diglycidyl ether afforded a SMART membrane having a structure of:

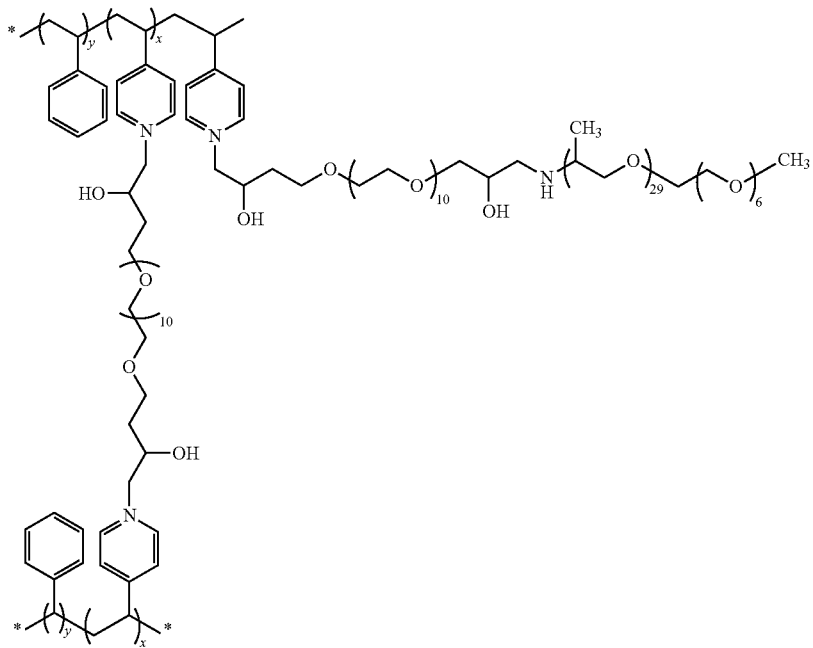

SMART In Vivo Glucose Sensors

In vivo glucose sensors having a working electrode with a glucose oxidase (GOX) enzyme layer were coated with the SMART membrane of poly(4-vinylpyridine-co-styrene) polymer and a polyetheramine crosslinker. The SMART membrane formulation was coated onto the enzyme layer by dipping the working electrode into the SMART membrane solution at a rate of 50 mm/sec.

Testing Method

The in vivo glucose sensors were tested in 0.1 M PBS buffer containing 10 mM glucose over a period 6 hours at temperatures ranging from 27° C. to 42° C. The temperature was controlled by a circulated water system with a digital temperature controller.

Figure 5:
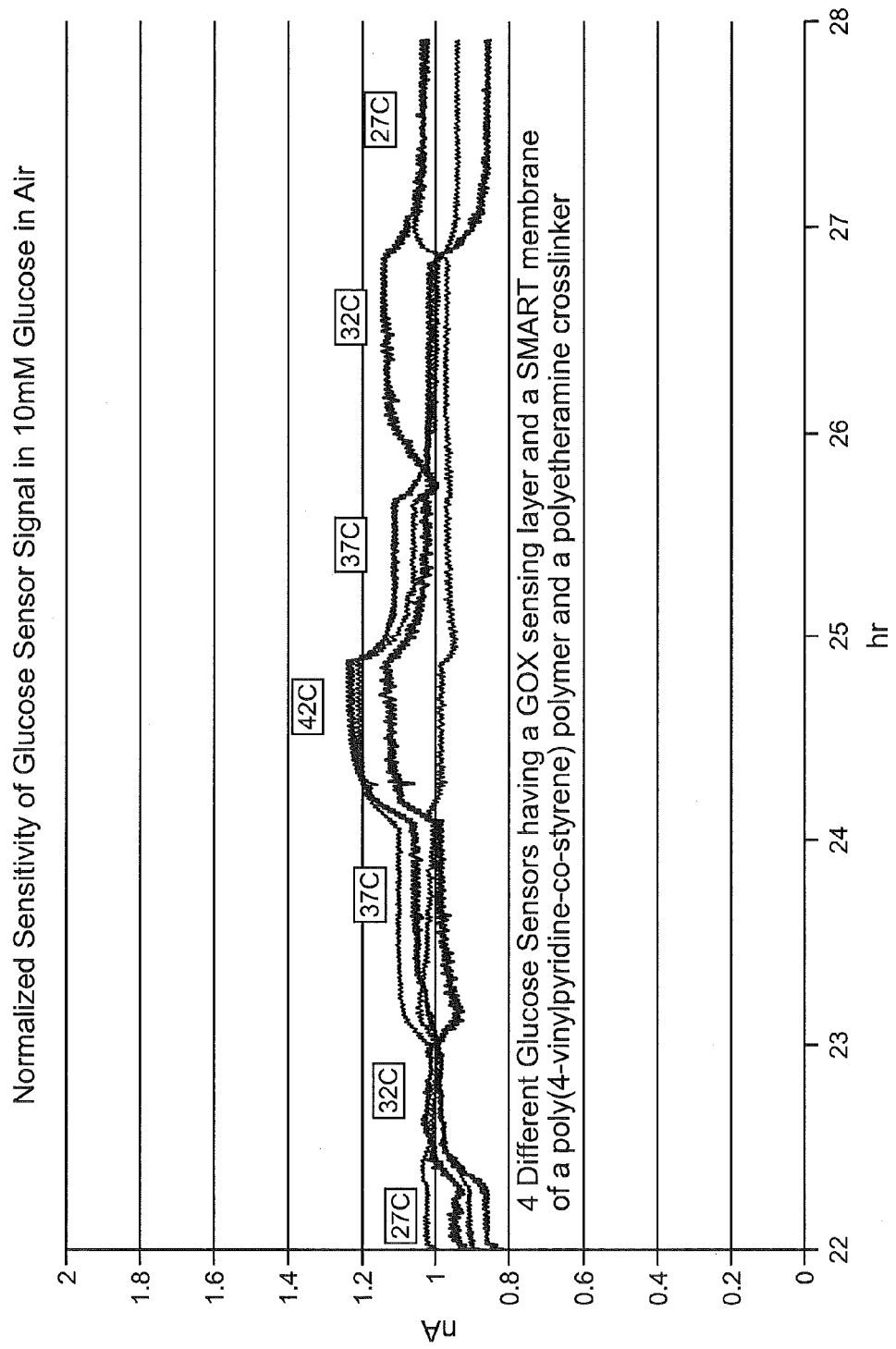
FIG. 5 shows a graph of normalized sensitivity of signal sensor over time at temperatures ranging from 27° C. to 42° C. for four different glucose sensors employing SMART membranes having a poly(4-vinylpyridine-co-styrene) polymer and polyetheramine crosslinker.

FIG. 5 depicts the change over time in normalized sensitivity of sensor signal at temperatures ranging from 27° C. to 42° C. for the in vivo glucose sensors employing a GOX enzyme layer and coated with a SMART membrane of poly(4-vinylpyridine-co-styrene) polymer and a polyetheramine crosslinker. As shown in FIG. 5 and summarized in Table 3 below, the glucose sensors having a GOX enzyme layer coated with SMART membranes exhibited changes in normalized sensitivity of sensor signal of 3.1% per ° C. or less over the tested temperature range. In some cases glucose sensors coated with SMART membranes exhibited changes in normalized sensitivity of sensor signal of 0.5% per ° C. or less. FIG. 5 further demonstrates that glucose sensors coated with SMART membranes are insensitive to changes in temperature. The percent increase per ° C. in normalized sensitivity of sensor signal of in vivo glucose sensors that included SMART membranes of a poly(4-vinylpyridine-co-styrene) polymer and a polyetheramine crosslinker under air is summarized in Table 3.

Figure 6:
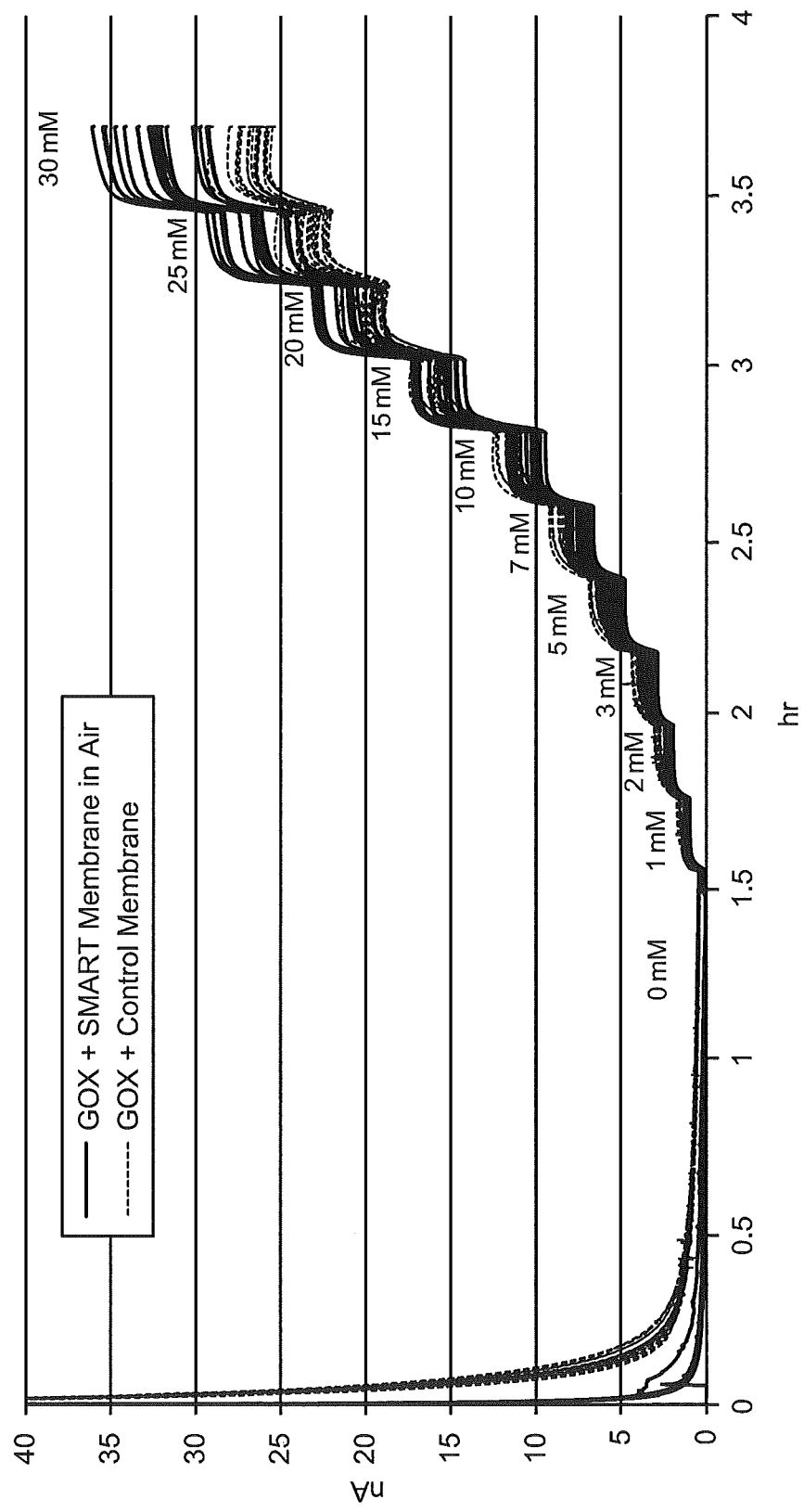
FIG. 6 shows a graph of sensor signal (in nA) over time (in hours) at different glucose concentrations (0 mM to 30 mM in phosphate buffer) comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane on the first day of continuous use.
Figure 7:
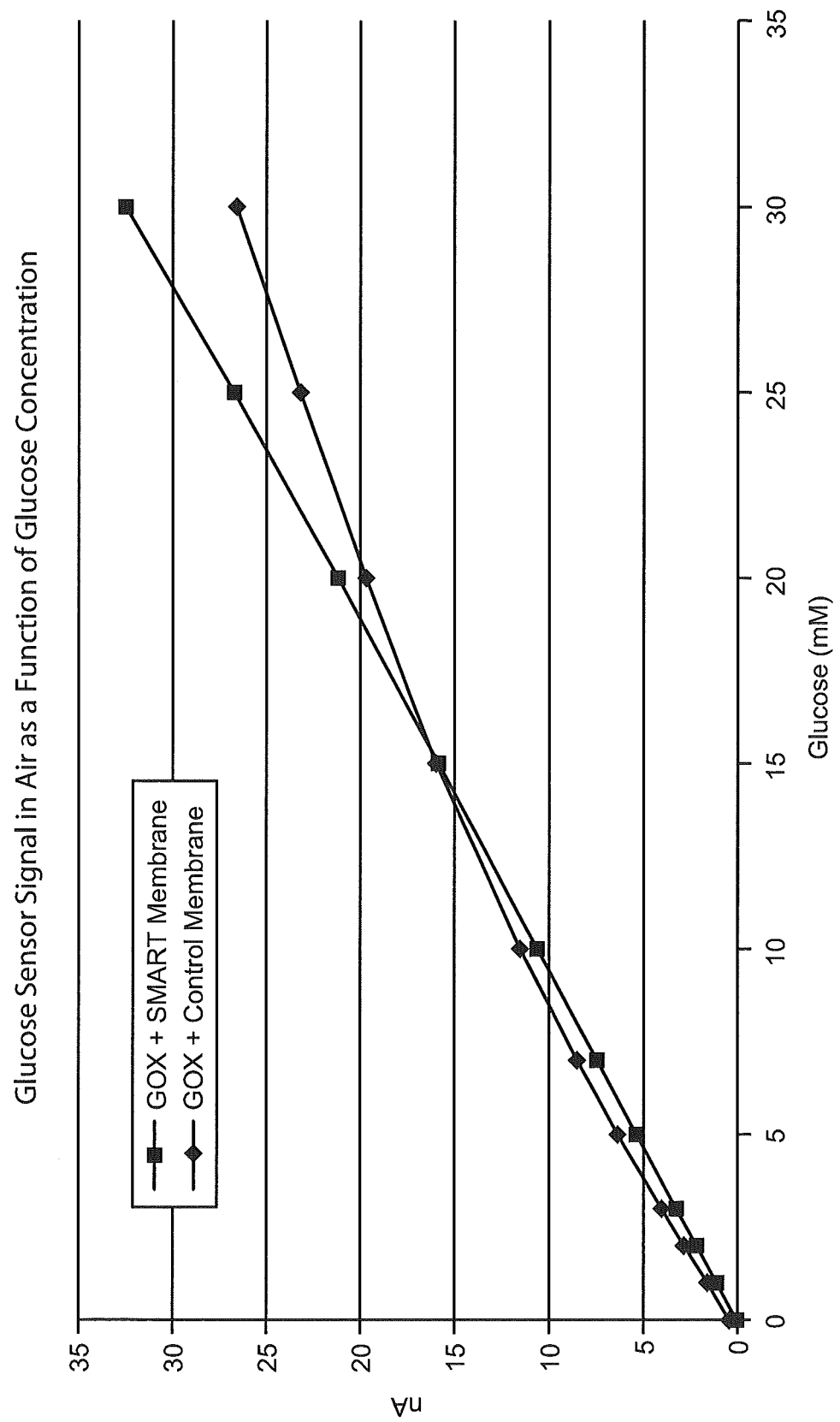
FIG. 7 shows a graph of sensor signal (in nA) as a function of glucose concentration (0 mM to 30 mM in phosphate buffer) comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane on the first day of continuous use.

FIG. 6 depicts the initial calibration of 16 different in vivo glucose sensors employing a GOX enzyme layer and coated with a SMART membrane of poly(4-vinylpyridine-co-styrene) polymer and a polyetheramine crosslinker with different concentrations of glucose in phosphate buffer. Calibration of control sensors employing a GOX enzyme layer and a poly(4-vinylpyridine-co-styrene) control polymer is also shown. Linearity of normalized sensor sensitivity is shown in FIG. 7 on the day of calibration of the in vivo glucose sensors that are coated with the SMART membranes as well as those coated with control membranes. As illustrated in FIG. 7, in vivo glucose sensors employing a GOX enzyme layer and coated with a SMART membrane of poly(4-vinylpyridine-co-styrene) polymer and a polyetheramine crosslinker exhibited linear sensor signal from 0 mM to 30 mM glucose concentration and showed higher normalized sensor sensitivity than control sensors in the range of concentrations ranging from 15 mM to 30 mM.

Figure 8:
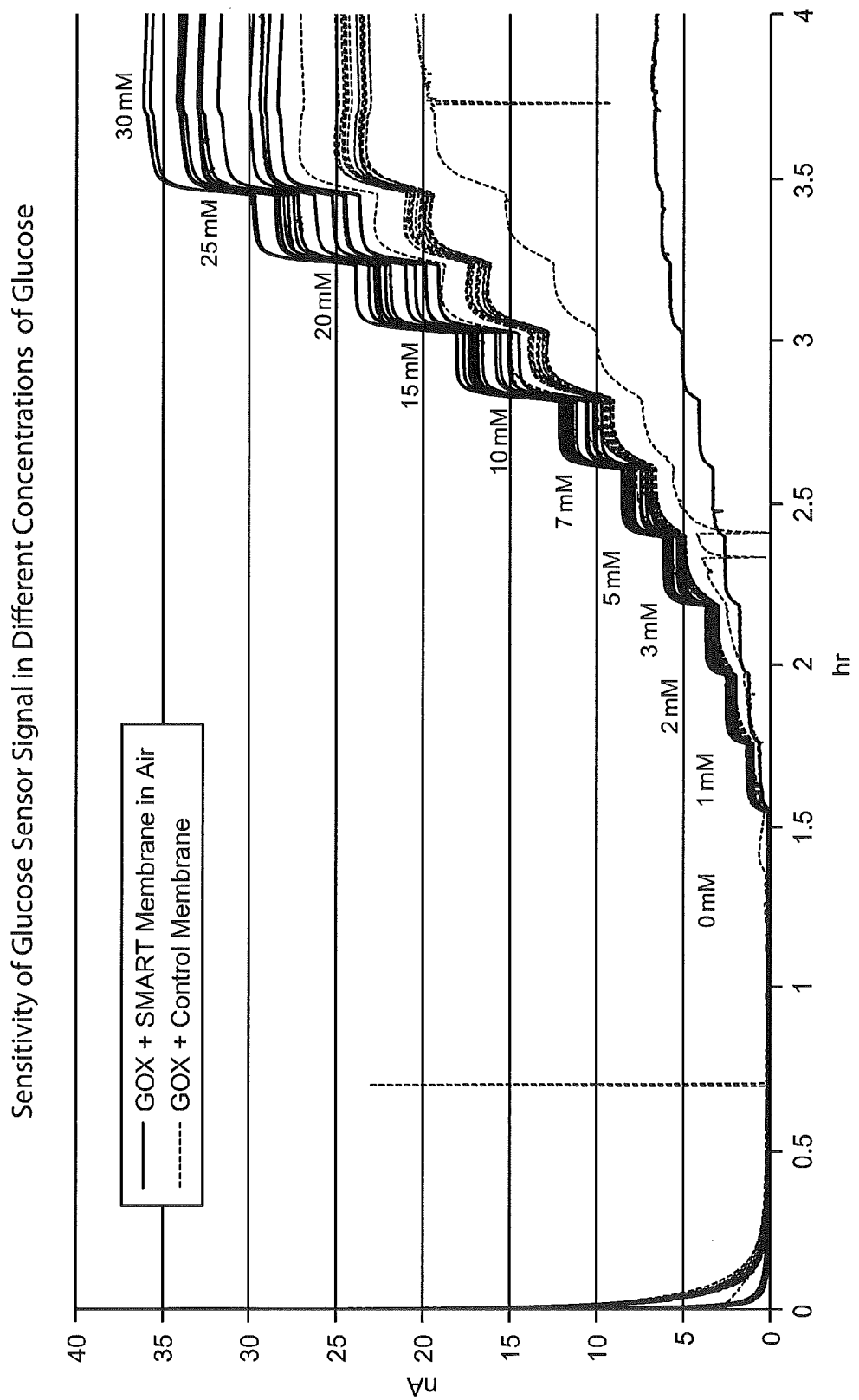
FIG. 8 shows a graph of sensor signal (in nA) over time (in hours) at different glucose concentrations (0 mM to 30 mM in phosphate buffer) comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane on the $14^{th}$ day of continuous use.
Figure 9:
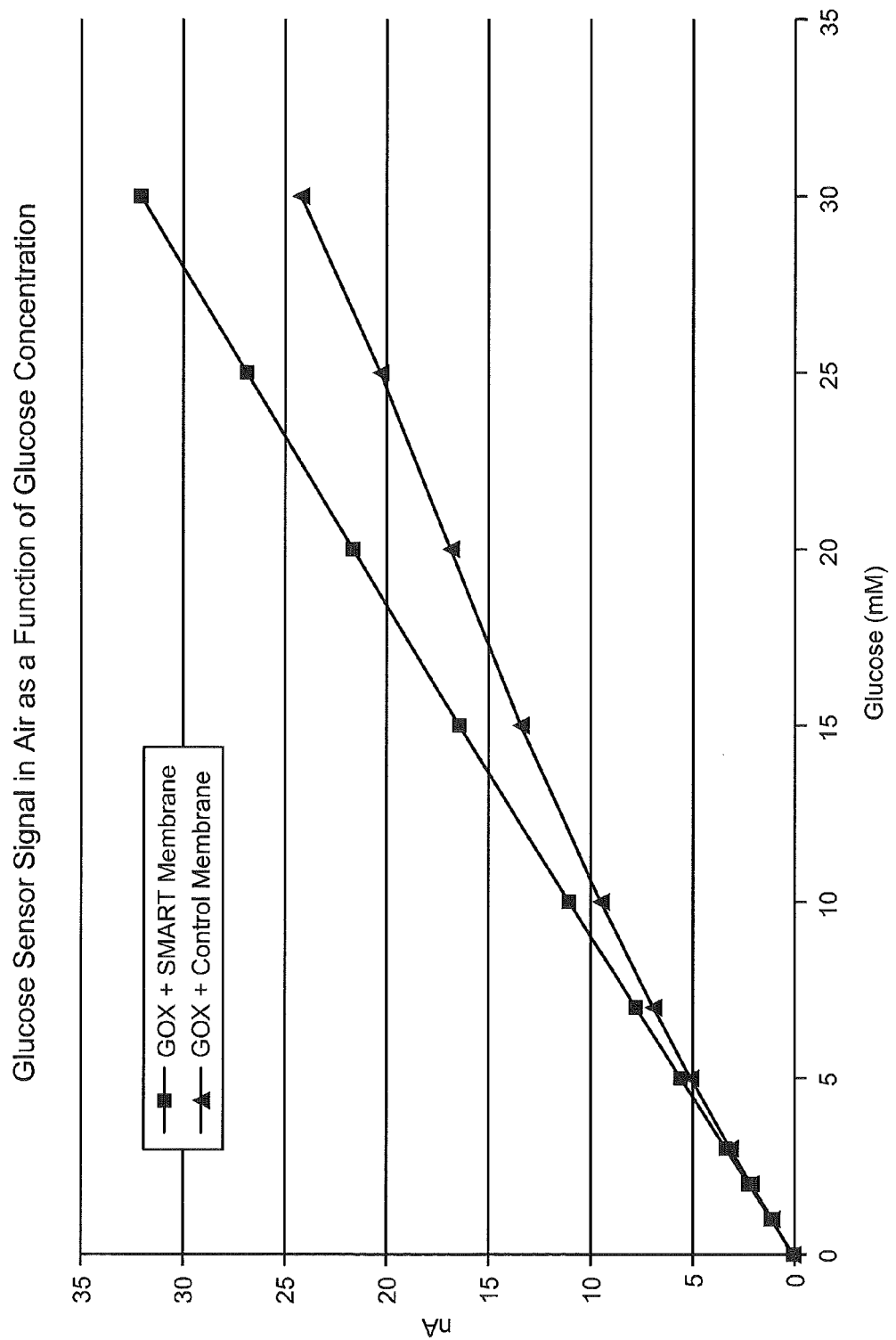
FIG. 9 shows a graph of sensor signal (in nA) as a function of glucose concentration (0 mM to 30 mM in phosphate buffer) comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane on the $14^{th}$ day of continuous use.

FIG. 8 depicts calibration of the in vivo glucose sensors after 14 days of continuous use with the same concentrations of glucose in phosphate buffer as used in initial sensor calibration. FIG. 9 compares the linearity of normalized sensor sensitivity after 14 days of continuous use of sensors employing a GOX enzyme layer and coated with a SMART membrane of poly(4-vinylpyridine-co-styrene) polymer and a polyetheramine crosslinker with sensors employing a GOX enzyme layer and coated with a poly(4-vinylpyridine-co-styrene) control polymer. As illustrated in FIG. 9, glucose sensors employing the SMART membrane exhibited linearity of sensor sensitivity signal from 0 mM to 30 mM and showed higher normalized sensor sensitivity than control sensors in the range of concentrations ranging from 5 mM to 30 mM.

Figure 10:
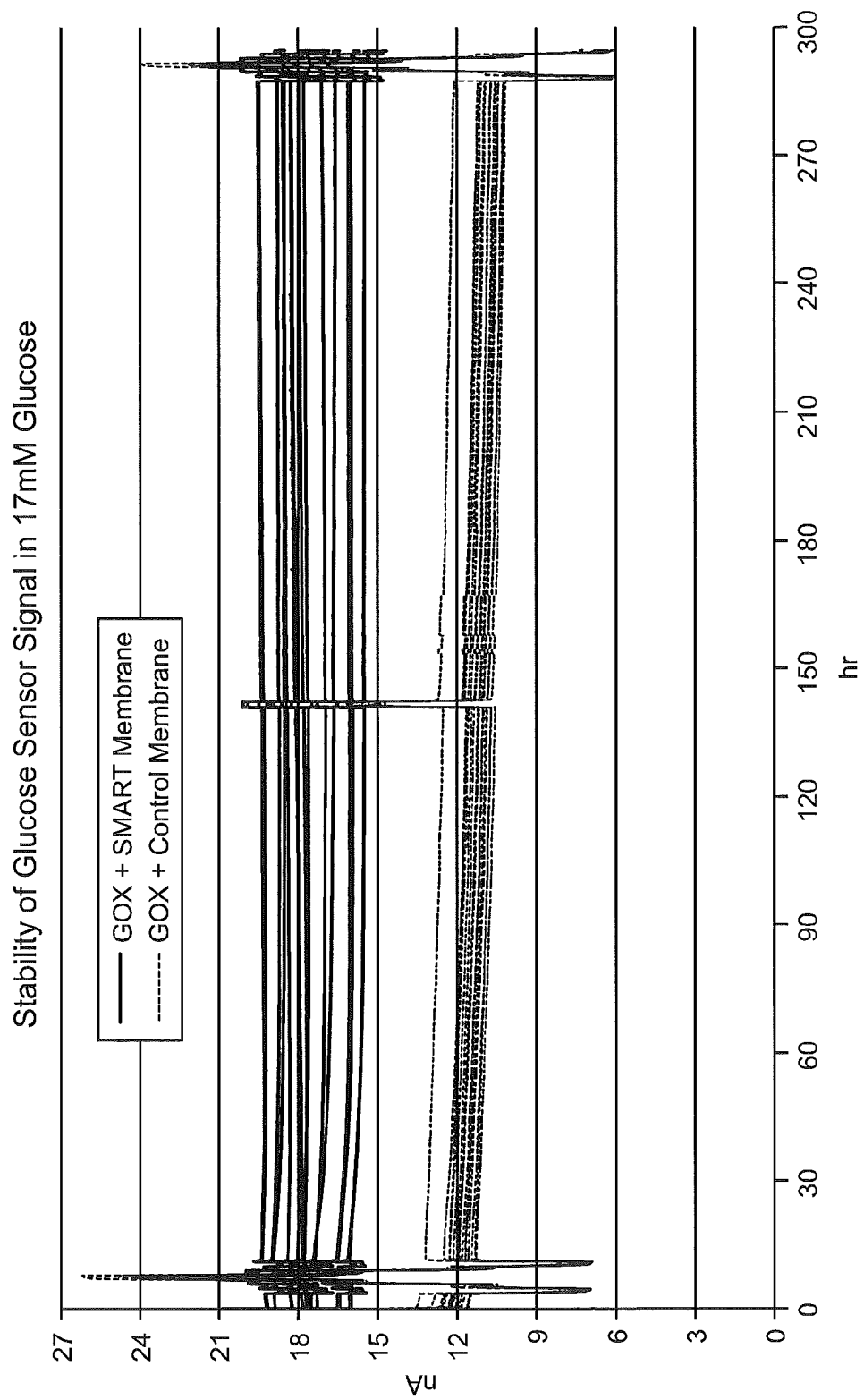
FIG. 10 shows a graph of sensor signal (in nA) stability over time at 33° C. in a solution having a glucose concentration of 17 mM comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane.

FIG. 10 compares the sensor signal as a function of time (in hours) of glucose sensors having SMART membranes to the control sensor in the 17 mM glucose solution at 33° C. As shown in FIG. 10, sensor signal for in vivo glucose sensors having SMART membranes were stable for well over 270 continuous hours. Sensor signal stability measured at the end of the study (after 296 hours) was found to be the same as at the commencement of the study.

Figure 11:
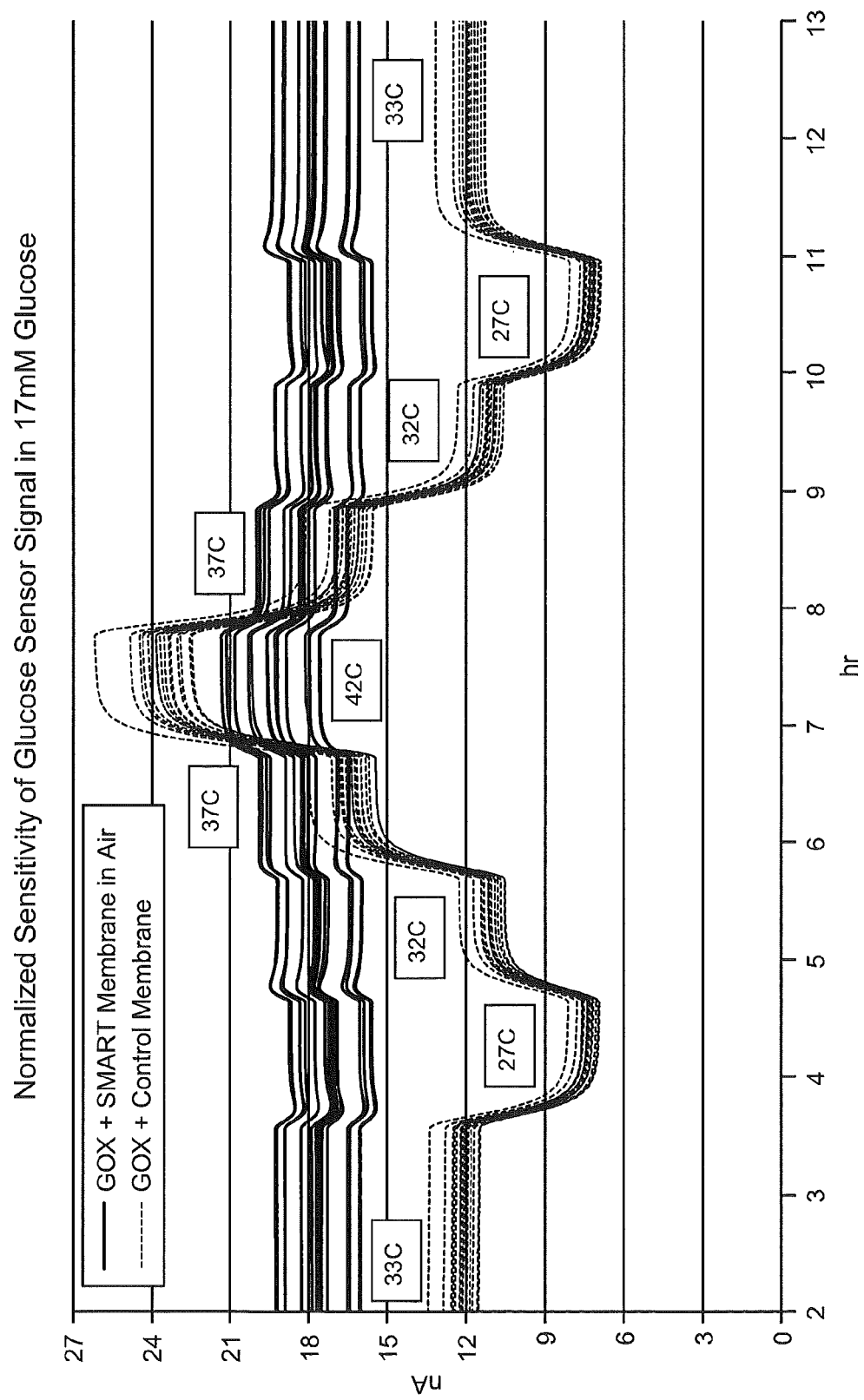
FIG. 11 shows a graph of normalized sensitivity of signal sensor in solution having a glucose concentration of 17 mM over time at temperatures ranging from 27° C. to 42° C. comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane on the first day of continuous use.
Figure 12:
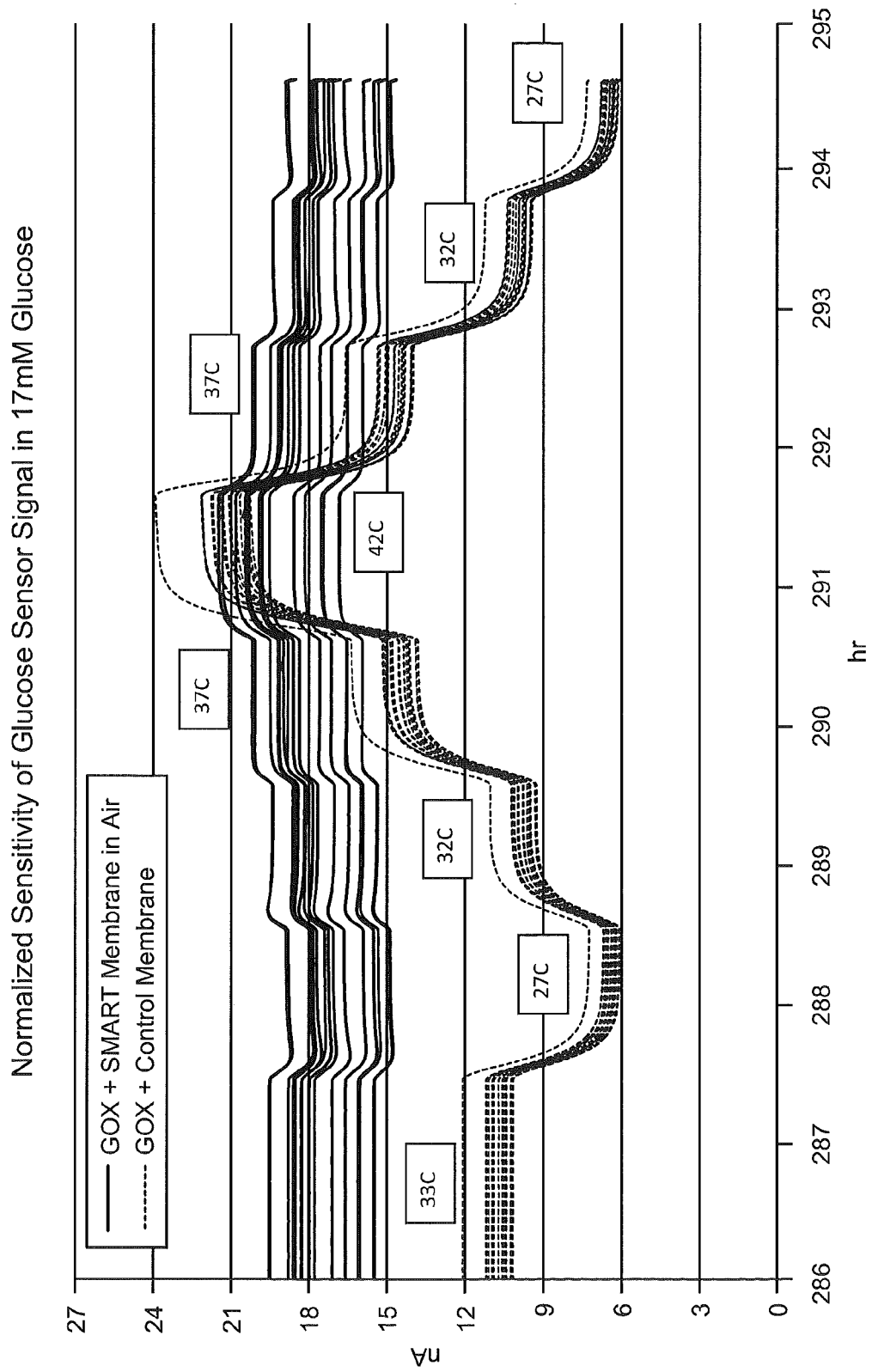
FIG. 12 shows a graph of normalized sensitivity of signal sensor in solution having a glucose concentration of 17 mM over time at temperatures ranging from 27° C. to 42° C. comparing glucose sensors employing SMART membranes having a poly(4-vinylpyridine-co-styrene) polymer and polyetheramine crosslinker and a glucose sensor employing a poly(4-vinylpyridine-co-styrene) polymer control membrane on the $14^{th}$ day of continuous use.

FIGS. 11 and 12 depict the change over time in normalized sensitivity of sensor signal at temperatures ranging from 27° C. to 42° C. for the SMART in vivo glucose sensors with the SMART membranes and the control glucose sensor over the course of 14 continuous days with hours 1 to 13 shown in FIG. 11 and hours 285 to 295 shown in FIG. 12. FIGS. 11 and 12 demonstrate that glucose sensors coated with SMART membranes exhibited little to no change in normalized sensitivity of sensor signal over the range of temperatures tested, whereas control sensors exhibited much larger temperature sensitivity, in particular at temperatures between 27° C. and 32° C. as well as between 37° C. and 42° C.

TABLE 3

| Sensor/ Membrane Type | % Increase per ° C. under Air | | | | | | | | | | | |
|---|---|---|---|---|---|---|---|---|---|---|---|---|
| | 27° C. to 32° C. | | 32° C. to 37° C. | | 37° C. to 42° C. | | 42° C. to 37° C. | | 37° C. to 32° C. | | 32° C. to 27° C. | |
| | individual | average | individual | average | individual | average | individual | average | individual | average | individual | average |
| GOX/ SMART membrane-1 | 3.5% | 3.1% | 1.3% | 1.1% | 2.8% | 2.8% | −2.7% | −2.7% | −0.9% | −1.2% | −2.8% | −2.8% |
| GOX/ SMART membrane-1 | 3.0% | | 1.1% | | 2.8% | | −2.7% | | −1.5% | | −3.0% | |
| GOX/ SMART membrane-1 | 2.8% | | 0.8% | | 2.7% | | −2.6% | | −1.3% | | −2.8% | |
| GOX/ SMART membrane-2 | 2.8% | 1.0% | −0.5% | 0.1% | 3.0% | 2.7% | −2.9% | −1.8% | 1.0% | 2.2% | −2.6% | −1.8% |
| GOX/ SMART membrane-2 | 2.4% | | −0.9% | | 2.7% | | −2.2% | | 0.5% | | −1.4% | |
| GOX/ SMART membrane-2 | −2.6% | | 1.8% | | 2.5% | | 0.0% | | 7.3% | | −1.1% | |

TABLE 3-continued

| Sensor/Membrane Type | % Increase per ° C. under Air | | | | | | | | | | | |
|---|---|---|---|---|---|---|---|---|---|---|---|---|
| | 27° C. to 32° C. | | 32° C. to 37° C. | | 37° C. to 42° C. | | 42° C. to 37° C. | | 37° C. to 32° C. | | 32° C. to 27° C. | |
| | individual | average | individual | average | individual | average | individual | average | individual | average | individual | average |
| GOX/SMART membrane-2 | 1.6% | | 0.0% | | 2.8% | | −2.0% | | 0.0% | | −2.2% | |
| GOX/SMART membrane-3 | −0.2% | −0.4% | 0.2% | 0.2% | 0.0% | −0.6% | −0.8% | −0.2% | −0.2% | 0.1% | 1.3% | 1.1% |
| GOX/SMART membrane-3 | −0.9% | | 0.0% | | −2.4% | | 1.5% | | 1.2% | | 1.8% | |
| GOX/SMART membrane-3 | 0.0% | | 0.4% | | 1.1% | | −1.6% | | −0.8% | | 0.6% | |
| GOX/SMART membrane-3 | −0.4% | | 0.2% | | −1.1% | | −0.0% | | 0.2% | | 0.9% | |
| GOX/SMART membrane-4 | 2.2% | 1.8% | 2.3% | 1.9% | 2.4% | 2.3% | −2.3% | −2.1% | −2.1% | −1.7% | −2.0% | −1.5% |
| GOX/SMART membrane-4 | 1.6% | | 1.8% | | 2.0% | | −1.8% | | −1.6% | | −1.4% | |
| GOX/SMART membrane-4 | 1.8% | | 2.0% | | 2.3% | | −1.9% | | −1.5% | | −1.3% | |
| GOX/SMART membrane-4 | 1.8% | | 1.6% | | 2.6% | | −2.4% | | −1.5% | | −1.3% | |

Sensors that include SMART membranes having a poly(4-vinylpyridine-co-styrene) polymer and a polyetheramine crosslinker exhibited little to no temperature sensitivity where sensor signals showed changes of less than 1%/° C., as well as linearity as a function of glucose concentration in solutions having concentrations of 0-30 mM and beaker stability for up to 10 days.

Example 3

In Vivo Glucose Sensors Having Membranes with a Branched Poly(4-vinylpyridine-co-styrene) Polymer and a Polyetheramine Crosslinker A branched SMART membrane that included a poly(4-vinylpyridine-co-styrene) polymer and polyetheramine crosslinker was prepared and tested as follows.

SMART Membrane Formulation

SMART membranes fabricated by crosslinking for 1 day, 2 days and 3 days were prepared and tested. For SMART membranes fabricated by crosslinking for three days, for the polyetheramine crosslinker solution, 0.1 mL of a 800 mg/mL PEG 550 diamine in 80% ethanol/20% of 10 mM HEPES was combined with 0.4 mL of a 400 mg/mL polyoxypropylenediamine in 80% ethanol/20% of 10 mM HEPES and 0.5 mL of a 210 mg/mL triglycidyl glycerol in 80% ethanol/20% of 10 mM HEPES and mixed for 3 days at room temperature.

For SMART membranes fabricated by crosslinking for two days, for the polyetheramine crosslinker solution, 0.4 mL of a 500 mg/mL PEG 550 diamine in 80% ethanol/20% of 10 mM HEPES was combined with 0.1 mL of a 1000 mg/mL polyoxypropylenediamine in 80% ethanol/20% of 10 mM HEPES and 0.5 mL of a 262 mg/mL triglycidyl glycerol in 80% ethanol/20% of 10 mM HEPES and mixed for 2 days at room temperature.

For SMART membranes fabricated by crosslinking for one day, polyetheramine crosslinker solution, 0.4 mL of a 600 mg/mL PEG 550 diamine in 80% ethanol/20% of 10 mM HEPES was combined with 0.1 mL of a 1200 mg/mL polyoxypropylenediamine in 80% ethanol/20% of 10 mM HEPES and 0.5 mL of a 315 mg/mL triglycidyl glycerol in 80% ethanol/20% of 10 mM HEPES and mixed for 2 days at room temperature.

For each type of SMART membranes (i.e., one-day, two-day and three-day formulations), 3 mL of a 150 mg/mL poly(4-vinylpyridine-co-styrene) solution in ethanol was added to 0.5 mL of the polyetheramine crosslinker solution with 10 L of a 100 mg/mL PDMS solution in ethanol and stirred for 2 days at 55° C. and drop wise the solution to 100 mL deionized water. The precipitate was collected and washed with deionized water and dried under vacuum.

SMART In Vivo Glucose Sensors

In vivo glucose sensors having a working electrode that includes glucose oxidase (GOX) in the enzyme layer were coated with the SMART membrane described above. The SMART membrane formulation was coated onto the enzyme areas of the in vivo glucose sensors by dipping the respective working electrodes into the ethanol/Hepes solution of poly(4-vinylpyridine-co-styrene) polymer polyetheramine crosslinker at a rate of 3×3 mm/sec producing a SMART membrane having a thickness of 30 μm.

Testing Method

The in vivo glucose sensors were tested in phosphate buffer (PBS) buffer containing 10 mM glucose at temperatures ranging from 27° C. to 42° C. The temperature was controlled by a circulated water system with a digital temperature controller. Table 4 summarizes the normalized sensitivity of sensor signals for each of the sensors fabricated.

TABLE 4

| Sensor/Membrane Type | Average Current at Different Temperatures (nA, 10 mM glucose) | | | | % Increase per ° C. under Air | | |
|---|---|---|---|---|---|---|---|
| | 37° C. | 42° C. | 27° C. | 37° C. | 37° C. to 42° C. | 42° C. to 27° C. | 27° C. to 32° C. |
| GOX/SMART membrane 3-day Crosslinking Sensor 1 | 12.6 | 13.3 | 10.3 | n/a | 1.1% | 1.7% | n/a |
| GOX/SMART membrane 3-day Crosslinking Sensor 2 | 13.5 | 14.2 | 10.6 | n/a | 1.1% | 1.9% | n/a |
| GOX/SMART membrane 2-day Crosslinking | 15.9 | 15.9 | 15.3 | 14.8 | 0.07% | 0.23% | 0.32% |
| GOX/SMART membrane 1-day Crosslinking | 15.9 | 15.9 | 15.3 | 14.8 | 0.07% | 0.23% | 0.32% |

Example 4

In Vivo Glucose Sensors Having Membranes with a Copolymer of Poly(4-vinylpyridine-co-styrene) and Polyethylene Oxide-Polypropylene Oxide (PEO-PPO)

Experiments were performed to test membrane formulations that included a copolymer of poly(4-vinylpyridine-co-styrene) and polyethylene oxide-polypropylene oxide. The SMART membrane was prepared and tested as follows.
SMART Membrane Formulation
A schematic of this reaction is shown in Scheme 3:

ylene oxide-polypropylene oxide. The SMART membrane formulation was coated onto the enzyme layer of the in vivo glucose sensor by dipping the respective working electrodes into the solution a copolymer of poly(4-vinylpyridine-co-styrene) and polyethylene oxide-polypropylene oxide at a rate of 50 mm/sec. A control sensor was prepared by coating a poly(4-vinylpyridine-co-styrene) polymer membrane onto a working electrode having a GOX enzyme layer.
Testing Method
The in vivo glucose sensors were tested in 0.1 M phosphate buffer (PBS) buffer containing 20 mM glucose at

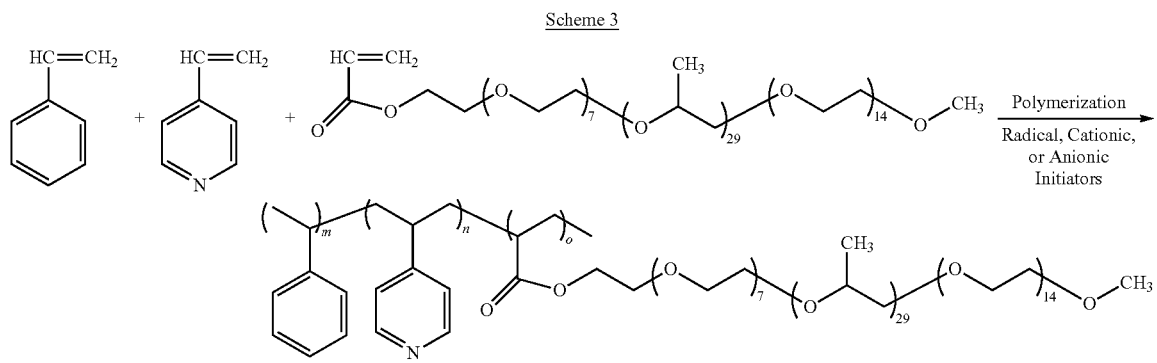

Scheme 3

Figure 13:
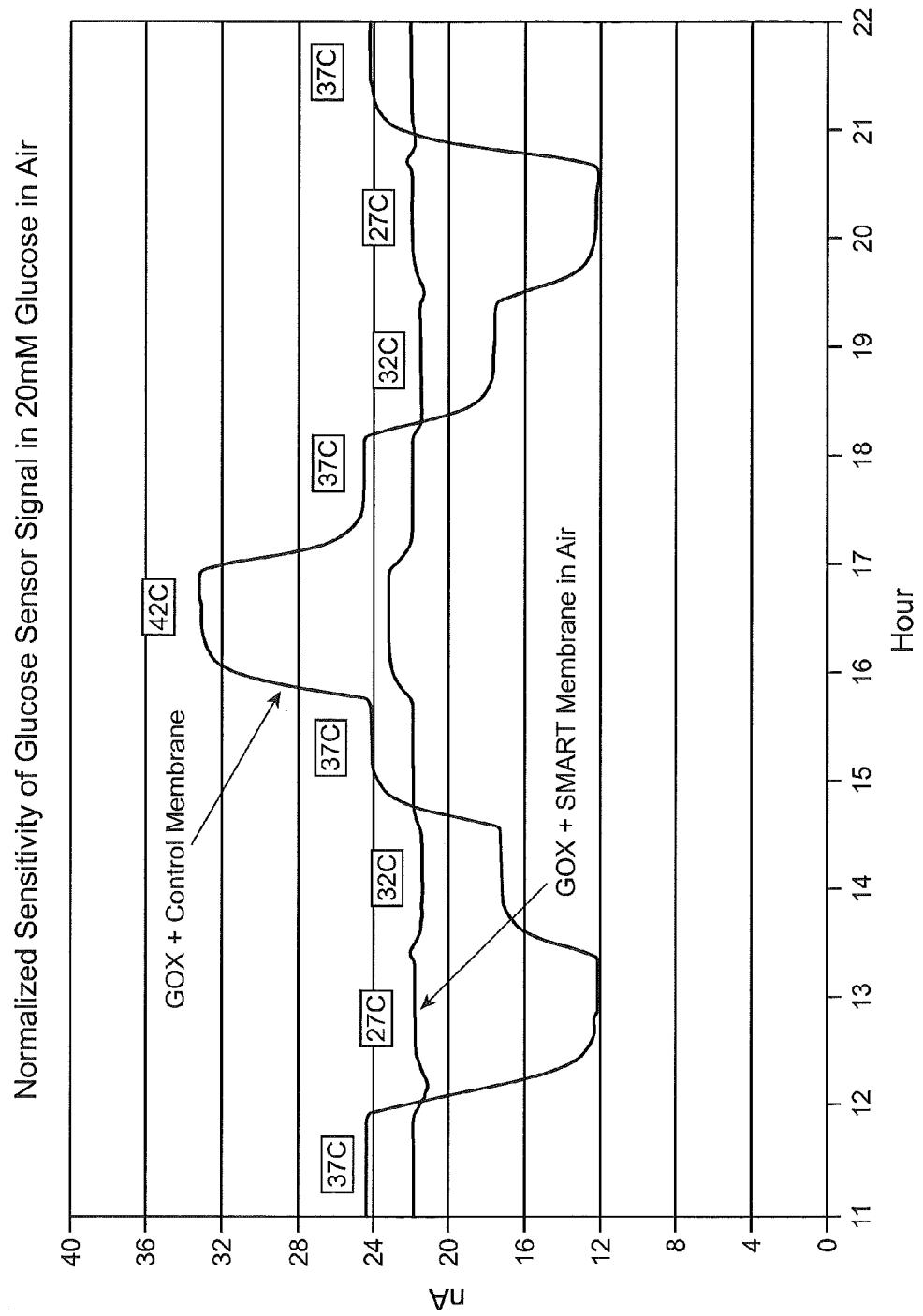
FIG. 13 shows a graph of normalized sensitivity of signal sensor in solution having a glucose concentration of 20 mM over time at temperatures ranging from 27° C. to 42° C. comparing glucose sensors employing SMART membranes having a copolymer of poly(4-vinylpyridine-co-styrene) and polyethylene oxide-polypropylene oxide and a glucose sensor employing a poly(4-vinylpyridine-co-styrene) polymer control membrane.

In Vivo Glucose Sensors
In vivo glucose sensors having a working electrode that includes glucose oxidase (GOX) in the enzyme layer were coated with SMART membrane formulation of a copolymer of poly(4-vinylpyridine-co-styrene) and polyethtemperatures ranging from 27° C. to 42° C. The temperature was controlled by a circulated water system with a digital temperature controller.
FIG. 13 depicts the change over time in normalized sensitivity of sensor signal at temperatures ranging from 27°

C. to 42° C. for the SMART in vivo glucose sensors with a SMART membrane of a copolymer of poly(4-vinylpyridine-co-styrene) and polyethylene oxide-polypropylene oxide and the control glucose sensor. FIG. 13 demonstrates that glucose sensors coated with SMART membranes exhibited little to no change in normalized sensitivity of sensor signal over the range of temperatures tested, whereas control sensors exhibited much larger temperature sensitivity, in particular at temperatures between 27° C. and 32° C. as well as between 37° C. and 42° C.

Table 5 below summarizes the normalized sensitivity of sensor signal depicted in FIG. 13. The data in Table 5 demonstrates that the glucose sensor coated with the SMART membrane of a copolymer of poly(4-vinylpyridine-co-styrene) and polyethylene oxide-polypropylene oxide exhibited a change in normalized sensitivity of sensor signal of 1.0% per ° C. or less (in some cases of less than 0.5% per ° C.) over the tested temperature range. In contrast, the control sensor having a enzyme layer of GOX coated with the poly(4-vinylpyridine-co-styrene) control membrane exhibited changes in normalized sensitivity of sensor signal of as high as 7.1% per ° C. over the same tested temperature range.

TABLE 5

| Sensor/ Membrane Type | % Increase per ° C. under Air | | | | | |
|---|---|---|---|---|---|---|
| | 27° C. to 32° C. | 32° C. to 37° C. | 37° C. to 42° C. | 42° C. to 37° C. | 37° C. to 32° C. | 32° C. to 27° C. |
| GOX/Control Membrane | 7.20% | 7.00% | 6.60% | −5.90% | −6.50% | −7.10% |
| GOX/PVPSty-PEO-PPO SMART membrane | −0.50% | 0.50% | 1.10% | −1.20% | −0.40% | 0.50% |

Figure 14:
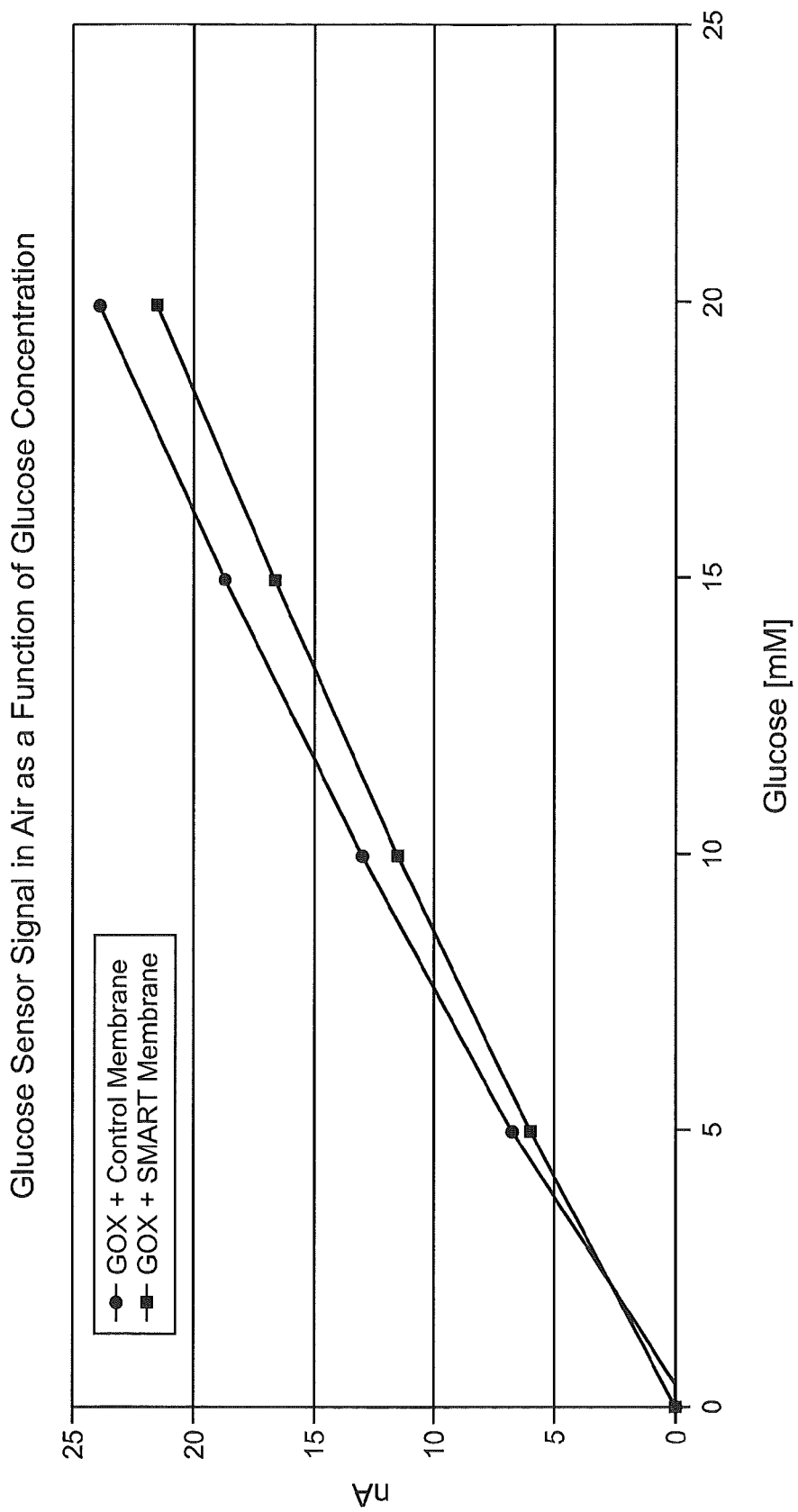
FIG. 14 shows a graph of sensor signal (in nA) as a function of glucose concentration (0 mM to 20 mM in phosphate buffer) comparing glucose sensors employing SMART membranes having a copolymer of poly(4-vinylpyridine-co-styrene) and polyethylene oxide-polypropylene oxide and a glucose sensor employing a poly(4-vinylpyridine-co-styrene) polymer control membrane.

The in vivo glucose sensors having SMART membranes of a copolymer of poly(4-vinylpyridine-co-styrene) and polyethylene oxide-polypropylene oxide exhibited good stability and linearity as a function of glucose concentration over a range from 0 mM to 20 mM. FIG. 14 depicts a graph comparing the sensor signal (in nA) of an in vivo glucose sensor employing a SMART membrane to a control glucose sensor as tested in PBS having a glucose concentration ranging 0 mM to 20 mM. As shown in FIG. 14, the sensor signals for sensors employing the SMART membranes were linear over the tested concentration range.

Figure 15:
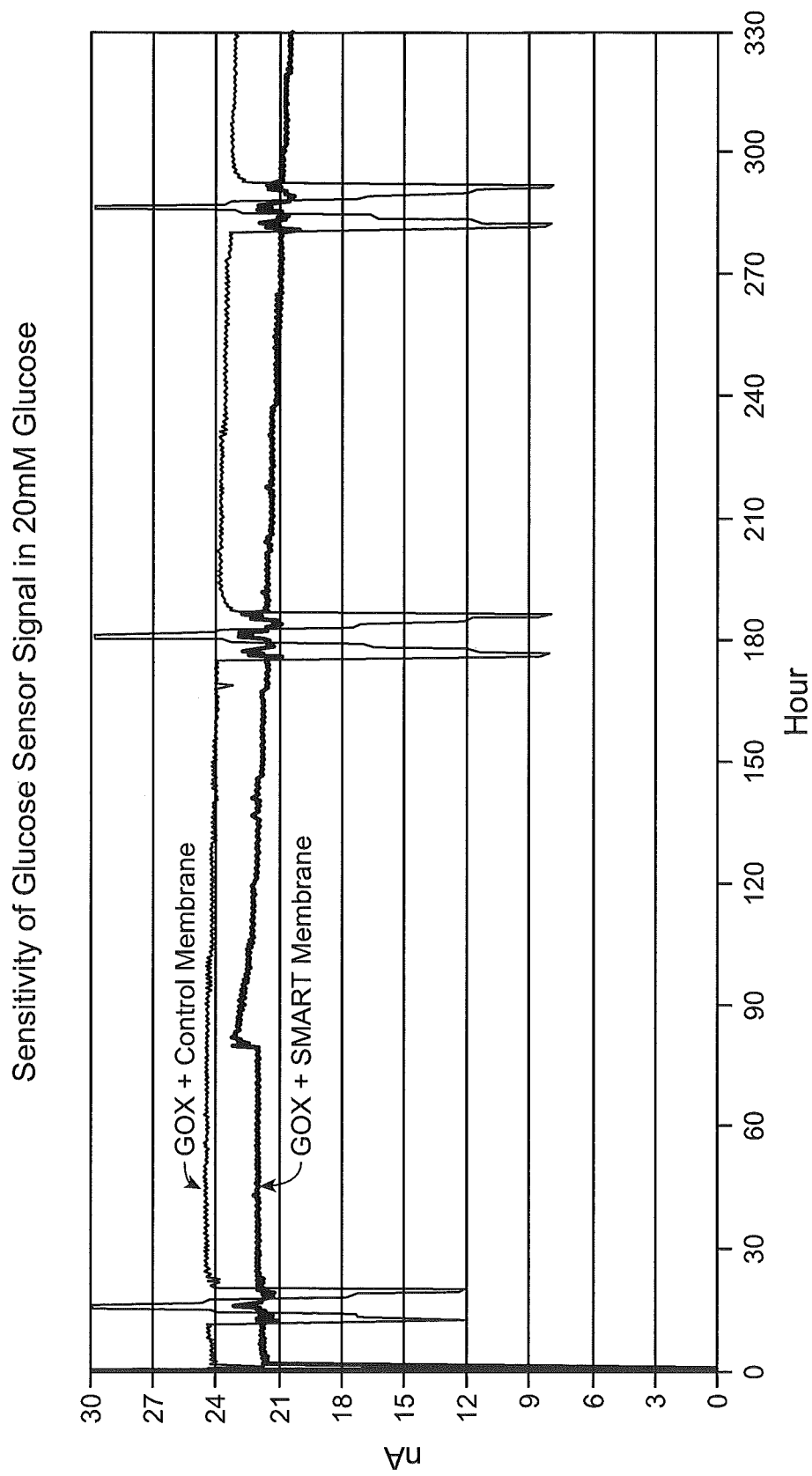
FIG. 15 shows a graph of sensor signal (in nA) stability over time at 37° C. in a solution having a glucose concentration of 20 mM comparing glucose sensors employing SMART membranes having a copolymer of poly(4-vinylpyridine-co-styrene) and polyethylene oxide-polypropylene oxide and a glucose sensor employing a poly(4-vinylpyridine-co-styrene) polymer control membrane.

The in vivo glucose sensors having a SMART membrane of a copolymer of poly(4-vinylpyridine-co-styrene) and polyethylene oxide-polypropylene oxide also showed good stability at 37° C. for over 300 hours of continuous use. Sensor signal was monitored by placing the sensor in a beaker of 20 mM glucose in phosphate buffer while stirring for a period of 330 hours. FIG. 15 depicts a graph comparing the sensor signal as a function of time (in hours) of a glucose sensor having a SMART membrane of a copolymer of poly(4-vinylpyridine-co-styrene) and polyethylene oxide-polypropylene oxide to a control sensor in the 20 mM glucose solution. As shown in FIG. 15, sensor signal for the in vivo glucose sensor having a SMART membrane was stable for well over 300 continuous hours. Sensor signal stability measured at the end of the study (after 330 hours) was found to be the same as at the commencement of the study.

In vivo glucose sensors which include SMART membranes having a copolymer of poly(4-vinylpyridine-co-styrene) and polyethylene oxide-polypropylene oxide exhibited little to no temperature sensitivity and sensor signals showed changes of less than 1%/° C., as well as good linearity in glucose solutions having concentrations of 0-20 mM and good beaker stability for up to two weeks at 37° C.

That which is claimed is:

1. A membrane structure comprising:
an enzyme layer; and
a membrane disposed proximate the enzyme layer, wherein the membrane comprises:
a polymer comprising a heterocyclic nitrogen containing component; and
a monoamine polyetheramine component that is covalently bonded to the nitrogen of the heterocyclic nitrogen containing component of the polymer.

2. The membrane structure according to claim 1, wherein the heterocyclic nitrogen containing component comprising a heteroaromatic ring system.

3. The membrane structure of claim 1, wherein the polymer comprises a heterocyclic nitrogen containing component is a poly(4-vinylpyridine-co-styrene) polymer.

4. The membrane structure of claim 3, wherein the poly(4-vinylpyridine-co-styrene) polymer comprises a compound of the formula:

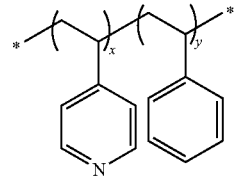

wherein x and y are each positive integers.

5. The membrane structure of claim 4, wherein the ratio of x and y is from 1:1 and 5:1.

6. The membrane structure of claim 1, wherein the monoamine polyetheramine component comprises a polyethylene oxide component and polypropylene oxide component.

7. The membrane structure of claim 6, wherein the molar ratio of the polypropylene oxide component and polyethylene oxide component is 1:35 to 35:1.

8. The membrane structure of claim 1, wherein the monoamine polyetheramine component has a molecular weight of 500 daltons to 5000 daltons.

9. The membrane structure of claim 1, wherein the monoamine polyetheramine component comprises a compound of the formula:

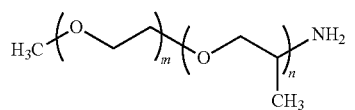
wherein n and m are each positive integers.
10. The membrane structure of claim 1, wherein the membrane is disposed on the enzyme layer.
* * * * *